United States Patent
Bunschoten et al.

(10) Patent No.: US 7,923,440 B2
(45) Date of Patent: Apr. 12, 2011

(54) METHOD OF TREATING OR PREVENTING IMMUNE MEDIATED DISORDERS AND PHARMACEUTICAL FORMULATION FOR USE THEREIN

(75) Inventors: Evert Johannes Bunschoten, Heesch (NL); Herman Jan Tijmen Coelingh Bennink, Driebergen (NL); Christian Franz Holinka, New York, NY (US)

(73) Assignee: Pantarhei Bioscience B.V. (NL)

( * ) Notice: Subject to any disclaimer, the term of this patent is extended or adjusted under 35 U.S.C. 154(b) by 657 days.

(21) Appl. No.: 10/517,686

(22) PCT Filed: Jun. 11, 2003

(86) PCT No.: PCT/NL03/00422
§ 371 (c)(1),
(2), (4) Date: Jun. 30, 2005

(87) PCT Pub. No.: WO03/103684
PCT Pub. Date: Dec. 18, 2003

(65) Prior Publication Data
US 2005/0261209 A1    Nov. 24, 2005

(30) Foreign Application Priority Data
Jun. 11, 2002    (EP) .................................... 02077272

(51) Int. Cl.
*A01N 45/00*    (2006.01)
*A61K 31/56*    (2006.01)
(52) U.S. Cl. ......... 514/169; 514/182; 514/874; 514/903
(58) Field of Classification Search ................... 514/182, 514/874, 903
See application file for complete search history.

(56) References Cited

U.S. PATENT DOCUMENTS

| | | | |
|---|---|---|---|
| 3,440,320 A | | 4/1969 | Sackler et al. |
| 3,797,494 A | | 3/1974 | Zaffaroni |
| 4,460,372 A | | 7/1984 | Campbell et al. |
| 4,573,996 A | | 3/1986 | Kwiatek et al. |
| 4,624,665 A | | 11/1986 | Nuwayser |
| 4,722,941 A | | 2/1988 | Eckert et al. |
| 4,762,717 A | | 8/1988 | Crowley, Jr. |
| 4,937,238 A | | 6/1990 | Lemon |
| 5,063,507 A | | 11/1991 | Lindsey et al. |
| 5,130,137 A | | 7/1992 | Crowley, Jr. |
| 5,211,952 A | | 5/1993 | Spicer et al. |
| 5,223,261 A | | 6/1993 | Nelson et al. |
| 5,340,584 A | * | 8/1994 | Spicer et al. .................. 424/426 |
| 5,340,585 A | | 8/1994 | Pike et al. |
| 5,340,586 A | | 8/1994 | Pike et al. |
| 5,468,736 A | | 11/1995 | Hodgen |
| 5,633,242 A | | 5/1997 | Oettel et al. |
| 5,662,927 A | | 9/1997 | Ehrlich et al. |
| 5,827,843 A | | 10/1998 | Koninckx |
| 6,214,815 B1 | | 4/2001 | Shangold et al. |
| 6,500,814 B1 | | 12/2002 | Hesch |
| 2002/0183299 A1 | * | 12/2002 | Voskuhl .................. 514/182 |

FOREIGN PATENT DOCUMENTS

| | | |
|---|---|---|
| DE | 2336433 A1 | 4/1975 |
| DE | 2336434 A1 | 4/1975 |
| DE | 2426779 A1 | 12/1975 |
| DE | 199 17 930 A1 | 10/2000 |
| EP | 0402950 A | 12/1975 |
| EP | 468690 A1 | 7/1991 |
| EP | 1700602 A1 | 5/2001 |
| WO | 9603929 A1 | 2/1966 |
| WO | 9218107 A1 | 10/1992 |
| WO | 9426207 | 11/1994 |
| WO | 9502408 A1 | 1/1995 |

(Continued)

OTHER PUBLICATIONS

Erdbruegger et al. Drug Discovery Today: Disease Mechanisms (2004), vol. 1, 73-81.*
Lab Tests Online (www.labtestsonline.org/understanding/conditions/autoimmune.html) retrived on Aug. 3, 2007.*
www.tiscali.co.uk/lifestyle/healthfitness/health_advice/netdoctor/archive/000489.html.*
MedlinePlus Medical Encyclopedia: Multiple Sclerosis, retrieved on Mar. 28, 2008 via www.nlm.nih.gov/medlineplus/ency/article/000737.htm, dated on Aug. 6, 2007.*

(Continued)

*Primary Examiner* — Sreeni Padmanabhan
*Assistant Examiner* — Mei-Ping Chui
(74) *Attorney, Agent, or Firm* — The Webb Law Firm

(57) ABSTRACT

A method of treating or preventing an immune mediated disorder in a mammal, said method comprising the administration of a therapeutically effective amount of an estrogenic component to said mammal, wherein the estrogenic component is selected from the group consisting of: substances represented by the following formula:

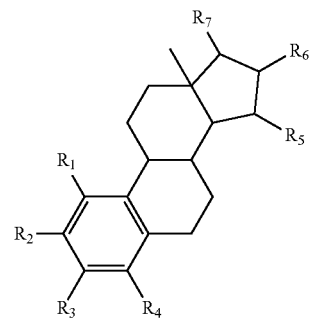

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; no more than 3 of $R_1$, $R_2$, $R_3$, $R_4$ are hydrogen atoms; precursors capable of liberating a substance according to the aforementioned formula when used in the present method; and mixtures of one or more of the aforementioned substances and/or precursors. Another aspect of the invention relates to a pharmaceutical formulation comprising the aforementioned estrogenic component, an immunotherapeutic agent and a pharmaceutically acceptable excipient.

12 Claims, 9 Drawing Sheets

FOREIGN PATENT DOCUMENTS

| | | |
|---|---|---|
| WO | WO 95/17895 | 7/1995 |
| WO | WO 9603929 A1 * | 2/1996 |
| WO | 9858657 A1 | 12/1998 |
| WO | 0062753 | 10/2000 |
| WO | WO 00/73416 | 12/2000 |
| WO | 0130357 A | 5/2001 |
| WO | WO 01/85154 A2 | 11/2001 |

OTHER PUBLICATIONS

WebMD: Multiple Sclerosis—Prevention, retrieved on Mar. 28, 2008 via www.webmd.com/multiple-sclerosis/tc/multiple-sclerosisms-prevention, dated on Mar. 23, 2006.*

MedlinePlus Medical Encyclopedia: rheumatoid arthritis, retrieved on Mar. 28, 2008 via www.nlm.nih.gov/medlineplus/ency/article/000431.htm, dated on Jul. 27, 2007.*

WebMD: Rheumatoid Arthritis—Prevention, retrieved on Mar. 28, 2008 via www.webmd.com/rheumatoid-arthritis/tc/rheumatoid-arthritis-prevention, dated on Aug. 23, 2006.*

Prophylactic definition—Medical Dictionary of Popular Medical Terms: retrieved on Mar. 14, 2008 via www.medterms.com/script/main/art.asp?articlekey=11902.*

MedlinePlus Medical Encyclopedia: Multiple Sclerosis, retrieved on Mar. 28, 2008 via www.nlm.nih.gov/medlineplus/ency/article/000737.htm, dated on Aug. 6, 2007, p. 1 and 2.*

MedlinePlus Medical Encyclopedia: Multiple Sclerosis, retrieved on Mar. 28, 2008, p. 2; also see WebMD: Multiple Sclerosis—Prevention, retrieved on Mar. 28, 2008 via www.webmd.com/multiple-sclerosis/tc/multiple-sclerosis-ms-prevention, dated on Mar. 23, 2006.*

MedlinePlus Medical Encyclopedia: rheumatoid arthritis, retrieved on Mar. 28, 2008 via www.nlm.nih.gov/medlineplus/ency/article/000431.htm, dated on Jul. 27, 2007, p. 1-2 and 4; also WebMD: Rheumatoid Arthritis—Prevention, retrieved on Mar. 28, 2008 via www.webmd.com/rheumatoid-arthritis/tc/rheumatoid-arthritis-prevention, dated on Aug. 23, 2006.*

Levine et al. (Am. J. Obstet. Gynecol. Mar. 15, 1984, p. 735-738).*

Allen et al., An Ovarian Hormone: Preliminary Report on Its Localization, Extraction and Partial Purification, and Action In Test Animals, JAMA, Sep. 8, 1923, vol. 81, pp. 819-821.

Allen et al., The Induction of a Sexually Mature Condition in Immature Females by Injection of the Ovarian Follicular Hormone, Am. J. Physiol., 1924, vol. 69, pp. 577-588.

Fishman, Fate of 15a-Hydroxyestriol-$^{3}$H in Adult Man, J. Clin. Endocrinol. Metab., 1970, vol. 31, pp. 436-438.

Jones et al., The Effects of Various Steroids on the Vaginal Histology in the Rat, Fertility and Sterility, Apr. 1973, vol. 24, No. 4, pp. 284-291.

Tulchinsky et al., Plasma Esterol as an Index of Fetal Well-Being, J. Clin. Endocrinol. Metab., 1975, vol. 40. pp. 560-567.

Tseng et al., Competition of Esterol and Ethynylestradiol with Estradiol for Nuclear Binding in Human Endometrium, Journal of Steroid Biochemistry, 1976, vol. 7, pp. 817-822.

Martucci et al., Uterine Estrogen Receptor Binding of Cathecholestrogens and of Esterol (1,2,5(10)-Estratriene-3,15a,16a,17 β-Tetrol), Steroids, Mar. 1976, vol. 27, No. 3, pp. 325-333.

Martucci et al., Direction of Estradiol Metabolism as a Control of its Hormonal Action—Uterotrophic Activity of Estradiol Metabolites, Endocrin., 1977, vol. 101, pp. 1709-1715.

Tseng et al., Heterogeneity of Saturable Estradiol Binding Sites in Nuclei of Human Endometrium Esterol Studies, Steroid Biochem., 1978, vol. 9, pp. 1145-1148.

Holinka et al., "in Vivo Effects of Esterol on the Immature Rat Uterus", Biology of Reproduction, Society for the Reproduction Society for the Study of Reproduction, Champaign, IL, US, Mar. 1979, vol. 20, No. 2, pp. 242-246.

Holinka, et al., "Comparison of Effects of Esterol and Tamoxifen with Those of Estriol and Estradiol on the Immature Rat Uterus", Biology of Reproduction, Society for the Reproduction Society for the Study of Reproduction, Champaign, IL, US, 1980, vol. 22, No. 4, pp. 913-926.

Jozan et al., Different Effects of Oestradiol, Oestriol, Oestrol and of Oestrone on Human Breast Cancer Cells (MCF-7) in Long Term Tissue Culture, Acta Endocrinologica, 1981, vol. 98, pp. 73-80.

Hammond et al., A Versatile Method for the Determination of Serum Cortisol Binding Globulin and Sex Hormone Binding Globulin Binding Capacities, 1983, vol. 132, pp. 101-110.

Levine et al., Uterine Vascular Effects of Esterol in Nonpregnant Ewes, Am. J. Obstet. Gynecol., 1984, vol. 148, No. 73. pp. 735-738.

Jansson et al., "Estrogen Induces a Potent Suppression of Experimental Autoimmune Encephalomyelitis and Collagen-Induced Arthritis in Mice", Journal of Neuroimmunology, Elsevier Science Publishers BV XX, 1994, vol. 53, No. 2, pp. 203-207.

Elger et al., Sulfamates of Various Estrogens are Prodrugs with Increased Systemic and Reduced Hepatic Estrogenicity at Oral Application, J. Steroid Biochem. Molec. Biol., 1995, vol. 55, No. 3 / 4, pp. 395-403.

Murphy et al., Endometrial Effects of Long-Term Low-Dose Administration of RU486, Fertility and Sterility, Apr. 1995, vol. 63, No. 4, pp. 761-766.

Reel et al., Survey and Assessment of Mammalian Estrogen Biological Assays for Hazard Characterization, Fundamental and Applied Toxicology, 1996, vol. 34, pp. 288-305.

Beral et al., Use of HRT and the Subsequent Risk of Cancer, Journal of Epidemiology and Biostatistics, 1999, vol. 4, No. 3, pp. 191-215.

Tavani et al., The Adverse Effects of Hormone Replacement Therapy, Drugs & Aging, May 1999, vol. 14, No. 5, pp. 347-357.

Pike et al., Progestins and Menopause: Epidemiological Studies of Risks of Endometrial and Breast Cancer, Steroids, 2000, vol. 65, pp. 359-664.

Avvakumov et al., Steroid-binding Specificity of Human Sex Hormon-binding Globulin is Influenced by Occupancy of a Zinc-binding Site, The Journal of Biological Chemistry, Aug. 25, 2000, vol. 275, No. 34, pp. 25920-25925.

Office Action mailed on Dec. 19, 2007 in U.S. Appl. No. 10/517,509.
Office Action mailed on Mar. 26, 2008 in U.S. Appl. No. 10/517,509.
Office Action mailed on Jan. 5, 2009 in U.S. Appl. No. 10/517,509.
Office Action mailed on Aug. 18, 2009 in U.S. Appl. No. 10/517,509.
Office Action mailed on Apr. 23, 2007 in U.S. Appl. No. 10/521,040.
Office Action mailed on Aug. 17, 2007 in U.S. Appl. No. 10/521,040.
Office Action mailed on Apr. 2, 2008 in U.S. Appl. No. 10/521,040.
Office Action mailed on Jun. 1, 2009 in U.S. Appl. No. 10/521,040.

Visser et al., "In vitro effects of estetrol on receptor binding, drug targets and human liver cell metabolism," CLIMACTERIC (2008) 11(1) Appx. II: 1-5.

Visser et al., "First human exposure to exogenous single-dose oral estetrol in early postmenopausal women," CLIMACTERIC (2008) 11(1): 1-10.

Visser et al., "Clinical applications of estetrol," J. Of Steroid Biochem and Molecular Biol. (2009) 114: 85-89.

Holinka et al., "Estetrol: A unique steroid in human pregnancy," J. of Steroid Biochem and Molecular Biol. (2009) 110: 138-143.

Coelingh Bennink et al., "Oral bioavailability and bone sparing effects of estetrol in an osteoporosis model," CLIMACTERIC (2008) 11 (Supp 3): 1-13.

Albertazzi Paola et al., "The Effect of Tibolone Versus Continuous Combined Norethisterone Acetate and Oestradiol on Memory, Libido and Mood of Postmenopausal Women: A Pilot study"; Database Biosis 'Online!; Oct. 31, 2000; pp. 223-229; vol. 36, No. 3; Biosciences Information Service, Philadelphia, PA., U.S.

Mueck et al., "Angio and Anti-Angiogenetic Effects of Estradiol and its Metabolites", J. Clin. Basic Cardiol., 2001, pp. 153-155, vol. 4, No. 2.

Shah et al., "Estrogen and Skin. An Overview", Am. J. Clin. Dermatol., 2001, pp. 143-150, vol. 2, No. 3.

Sitruk-Ware et al., "Local Hormonal Treatment for Urogenital Atrophy After Menopause", Shweiz. Rundsch. Med. Praxis, 1997, pp. 1245-1248, vol. 86, No. 33, and Sitruk-Ware, English Translation, 1997. Praxis, Schweizerische Rundschau fur Medizin, vol. 86, No. 33, pp. 1-13.

Schmidt et al., "Treatment of Skin Aging with Topical Estrogens", Int. J. Dermatol., 1996, pp. 669-674, vol. 35, No. 9.

Younglai et al., Journal of Clinical Endocrinology and Metabolism, 1968, vol. 28, Issue 11, pp. 1611-1617.

Webster Ninth New Collegiate Dictionary, 2000, Definition of Prevention, p. 1.
Willhite et al., Pharmacotherapy, 2001, vol. 21, Issue 4, pp. 464-480.
Seeger et al., "The inhibitory effect of endogenous estrogen metabolies on copper-mediated in vitro oxidation of LDL", Int. Journal of Clinical Pharmacology and Therapeutics, (1998), vol. 36, No. 7, pp. 383-385.
Kuipers et al., "Enterohepatic Circulation in the Rat", Gastroenterol., vol. 88, pp. 403-411 (1985).
Schwartz, "A Model for the Regulation of Ovulation in the Rat", Recent Prog. Horm. Res., vol. 25, pp. 1-55, (1969).
Beattie et al., "The Differential Effects of Diestrous Progestogen Administration on Proestrous Gonadotrophin Levels, Endocrinol", vol. 97, pp. 885-890, (1975).
De Visser et al., Endocrinological Studies with (7a, 17 a)-17-Hydroxy-7-me norpregn-5(10)-en-20-yn-3-one (Org OD 14), Arzneim, Forsh., vol. 34, pp. 1010-1020, (1984).
National Cancer Institute: Breast cancer prevention retrieved online Aug. 7, 2007 from the internet; http://www.cancer.gov/templates/doc.aspx?viewed=D972A74B-D25A-4F86-B8ED-33EB3C0450E4&version, p. 1.
Medline Plus: Medical Encyclopedia: Ovarian cancer retrieved online on Aug. 9, 2007 from the internet: https://www.nlm.nih.gov/medlineplus/ovariancancer.html, p. 1 dated Jul. 31, 2007.
National Institute of Child Health and Human Development, NIH Publication No. 02-2413 retrieved online on Aug. 9, 2007.
Breast Cancer Prevention retrieved online Aug. 7, 2007 from the internet; http://www.cancer.gov/cancertopics/pdq/prevention/breast/Patient/page 3.
Zips et al., in vivo, 2005, vol. 19, pp. 1-8.
Holinka et al., Biology of Reproduction, 1980, vol. 22, pp. 913-926.
Martucci et al., "Impact of Continuously Administered Catechol Estrogens on Uterine Growth and Luteinizing Hormone Secretion", Endocrinology (Dec. 1979), vol. 105, No. 6, pp. 1288-1292.
Weigert et al., "Comparison of Stimulation with Clomiphenes Citrate in Combination with Recombinant Follicle Stimulating Hormone and Recombinant Luteinizing Hormone to Stimulation with a Gonadotropin-Releasing Hormone Agonist Protocol: A Prospective Randomized Study", Fertility and Sterility, (Jul. 2002), vol. 78, No. 1, pp. 34-39.
Trotter et al., "Effects of Postnatal Estradiol and Progesterone Replacement in Extremely Preterm Infants", J. Clin. Endocrinol Metab., (Dec. 1999), vol. 84, No. 12, pp. 4531-4535.
Shanklin et al., "Aqueous Estrogens in the Management of Respiratory Distress SYndrome", J. Reprod. Med. (Aug. 1970), vol. 5, No. 2, pp. 53-71.
Chemical Abstracts Service, Columbus Ohio, US: Jakowicki, "Evaluation of Estriol Level in the Amniotic Fluid in Prolonged Pregnancy", XP002458625.
Gorwill et al., "Unconjugated Serum Oestriol Levels in Mother and Baby with Meconium Staining of the Amniotic Fluid", Br. J. Obstet. Gynaecol. (Aug. 1978), vol. 85, No. 8, pp. 602-604.
Fogary, Jr., "Postmaturity", J. Am. Osteopath. Assoc., (Jan. 1976), vol. 75, No. 5, pp. 512-517.
Office Action mailed on Jan. 11, 2008 in U.S. Appl. No. 10/478,262.
Office Action mailed on May 15, 2008 in U.S. Appl. No. 10/478,262.
Office Action mailed on Feb. 19, 2009 in U.S. Appl. No. 10/478,262.
Office Action mailed on Jun. 9, 2009 in U.S. Appl. No. 10/478,262.
Office Action mailed on Nov. 18, 2008 in U.S. Appl. No. 10/478,264.
Office Action mailed on May 22, 2009 in U.S. Appl. No. 10/478,264.
Office Action mailed on Mar. 17, 2008 in U.S. Appl. No. 10/478,357.
Office Action mailed on May 16, 2008 in U.S. Appl. No. 10/478,357.
Office Action mailed on Dec. 16, 2008 in U.S. Appl. No. 10/478,357.
Office Action mailed on May 28, 2009 in U.S. Appl. No. 10/478,357.
Office Action mailed on Apr. 6, 2007 in U.S. Appl. No. 10/478,365.
Office Action mailed on Sep. 7, 2007 in U.S. Appl. No. 10/478,365.
Office Action mailed on Apr. 1, 2008 in U.S. Appl. No. 10/478,365.
Office Action mailed on Jun. 8, 2009 in U.S. Appl. No. 10/478,365.
Office Action mailed on Jan. 24, 2007 in U.S. Appl. No. 10/495,707.
Office Action mailed on Dec. 28, 2007 in U.S. Appl. No. 10/495,707.
Office Action mailed on Aug. 19, 2008 in U.S. Appl. No. 10/495,707.
Office Action mailed on May 22, 2009 in U.S. Appl. No. 10/495,707.
Office Action mailed on Oct. 15, 2007 in U.S. Appl. No. 20/517,509.

* cited by examiner

METHOD OF TREATING OR PREVENTING IMMUNE MEDIATED DISORDERS AND PHARMACEUTICAL FORMULATION FOR USE THEREIN

TECHNICAL FIELD OF THE INVENTION

The present invention relates to a method for treating or preventing immune mediated disorders in a mammal by administering an effective amount of an estrogenic component to said mammal. The method is particularly suited for treating or preventing T lymphocyte-mediated disorders and/or chronic inflammatory diseases, including, but not limited to, autoimmune diseases, such as multiple sclerosis, rheumatoid arthritis, osteoarthritis, insulin dependent diabetes (type I diabetes), systemic lupus erythrematosis and psoriasis. immune pathologies induced by infectious agents, such as helminthic (e.g., leishmaniasis) and certain viral infections, including HIV, and bacterial infections, including Lyme disease, tuberculosis and lepromatous leprosy, transplant rejection, graft versus host disease and atopic conditions, such as asthma and allergy, including allergic rhinitis, gastrointestinal allergies, including food allergies, eosinophilia, conjunctivitis and glomerular nephritis.

Another aspect of the invention is concerned with a pharmaceutical formulation for use in the aforementioned method, wherein the formulation comprises an estrogenic component, an immunotherapeutic agent and a pharmaceutically acceptable excipient.

BACKGROUND OF THE INVENTION

The role of female sex hormones in various immune mediated disorders has been the subject of various scientific publications. It has been recognised that autoimmune diseases such as multiple sclerosis and rheumatoid arthritis preferentially affect women (Jansson et al., Inflamm Res 1998 July; 47(7): 290-301). In addition the observation has been made that during pregnancy, when levels of female sex hormones are high, clinical remissions of cell-mediated autoimmune diseases are common, with disease exacerbation often seen post-partum when sex hormone levels are low (Kim et al., Neurology 1999 Apr. 12; 52(6) 1230-1238). Furthermore it has been reported that an unusually high fraction of patients with multiple sclerosis show decreased gonadotropin and estrogen values in the urine (Poser et al., Geburtshilfe Frauenhielkd 1981 May; 41(5): 353-358).

Furthermore studies in castrated mice have shown that administration of estradiol and estriol in an amount which induces the serum levels seen at late stage pregnancy, delays the onset of experimental autoimmune encephalomyelitis (EAE), a Th1 cell-dependent autoimmune disease used as a model of multiple sclerosis (Jansson et al., Inflamm Res 1998 July; 47(7): 290-301). The results of an evaluation of the effect of 17β-estradiol on gene expression in EAE using DNA microarray implicate a limited set of known and previously unsuspected estradiol-sensitive genes that may be crucial for inhibition of EAE and potentially the human disease, multiple sclerosis (Matejuk et al., Endocrinology 2002 January; 143 (1): 313-319).

WO 01/185154 relates to a method of ameliorating a Th1-mediated immune pathology in a mammal by administering a low dose of estrogen to the mammal, particularly a low dose of 17β-estradiol, estriol or estrone. Low doses of these estrogens are deemed necessary to avoid the potential adverse effects of high levels of estrogen on the reproductive and circulatory systems and also to prevent unwanted side effects in males.

The aforementioned estrogens 17β-estradiol, estriol and estrone have in common that they are endogenous to the female body, i.e. they are biogenic estrogens. These biogenic estrogens show serious pharmacokinetic deficits. Their oral bio-availability is very low and varies greatly from person to person, meaning that general dosage recommendations cannot be given. Fast elimination of these estrogens from the blood is another related problem. For instance, for the main human biogenic estrogen 17β-estradiol the half-life is around 1 hour. As a result, between separate (daily) administration events, blood serum levels of such biogenic estrogens tend to fluctuate considerably. Thus, shortly after administration the serum concentration is usually several times higher than the optimum concentration. In addition, if the next administration event is delayed, serum concentrations will quickly decrease to a level where the estrogen is no longer physiologically active.

In addition to pharmacokinetic problems, the known estrogens also show pharmacodynamic deficits. After resorption from the intestinal lumen, orally applied active ingredients enter the organism via the liver. This fact is of specific importance for estrogenic agents as the liver is a target organ for estrogens; oral intake of estrogens results in strong estrogenic effects in the liver. The secretion activity that is controlled by estrogens in the human liver includes increased synthesis of transport proteins CBG, SHBG, TBG, several factors that are important for the physiology of blood clotting, and lipoproteins. If biogenic estrogens are introduced to the female organism while avoiding passage through the liver (e.g. by transdermal application), the liver functions mentioned remain largely unchanged. Therapeutically equivalent doses of commonly known biogenic estrogens, when applied orally, result in clear responses of hepatic parameters, such as increase of SHBG, CBG, angiotensinogen and HDL (high density lipoprotein).

Consequently there is a need for estrogenic substances that:
(a) are more effective in a method of treating immune mediated diseases as the aforementioned biogenic estrogens and/or
(b) have a significantly longer halflife than the aforementioned biogenic estrogens and/or
(c) are orally administerable without causing significant hepatic effects and/or
(d) produce less undesirable side-effects than the aforementioned biogenic estrogens.

SUMMARY OF THE INVENTION

The inventors have surprisingly found that these requirements are met by estrogenic substances that are represented by the following formula

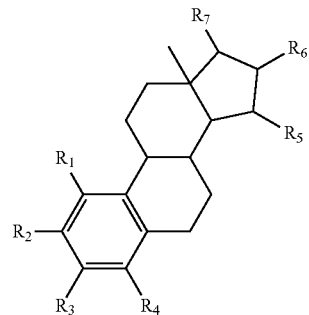

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms.

A known representative of this group of estrogenic substances is 1,3,5 (10)-estratrien-3,15α,16α,17β-tetrol, also known by the names of estetrol, oestrol and 15α-hydroxyestriol. Estetrol is an estrogen that is produced by the fetal liver during human pregnancy. Unconjugated estetrol levels in maternal plasma peak at about 1.2 ng/ml at term pregnancy and are about 12 times higher in fetal than in maternal plasma (Tulchinsky et al., 1975. J. Clin. Endocrinol. Metab., 40, 560-567).

In 1970, Fishman et al., "Fate of 15α-hydroxyestriol-$^3$H in Adult Man", J Clin Endocrinol Metab (1970) 31, 436-438, reported the results of a study wherein tritium labeled 15α-hydroxyestriol (estetrol) was administered intravenously to two adult women. It was found that the estetrol was rapidly and completely excreted in urine as the glucosiduronate and that virtually no metabolism except for conjugation took place.

Between 1975 and 1985 several researchers have investigated the properties of estetrol and reported on its estrogenic potency and uterotrophic activity. The most relevant to publications that were issued during this period are mentioned below:

Levine et al., 1984. Uterine vascular effects of estetrol in nonpregnant ewes. Am. J. Obstet. Gynecol., 148:73, 735-738: "When intravenously administered in nonpregnant ewes, estetrol is 15 to 30 times less potent than estriol and 17β-estradiol in uterine vasodilation".

Jozan et al., 1981. Different effects of oestradiol, oestriol, oestetrol and of oestrone on human breast cancer cells (MCF-7) in long term tissue culture. Acta Endocrinologica, 98, 73-80: "Estetrol agonistic potency is 2% of the magnitude observed for 17β-estradiol in in vitro cell proliferation".

Holinka et al., 1980. Comparison of effects of estetrol and tamoxifen with those of estriol and estradiol on the immature rat uterus. Biol. Reprod. 22, 913-926: "Subcutaneously administered estetrol has very weak uterotrophic activity and is considerable less potent than 17β-estradiol and estriol".

Holinka et al., 1979. In vivo effects of estetrol on the immature rat uterus. Biol. Reprod. 20, 242-246: "Subcutaneously administered estetrol has very weak uterotrophic activity and is considerable less potent than 17β-estradiol and estriol".

Tseng et al., 1978. Heterogeneity of saturable estradiol binding sites in nuclei of human endometrium. Estetrol studies. J. Steroid Biochem. 9, 1145-1148: "Relative binding of estetrol to estrogen receptors in the human endometrium is 1.5% of 17β-estradiol".

Martucci et al., 1977. Direction of estradiol metabolism as a control of its hormonal action-uterotrophic activity of estradiol metabolites. Endocrin. 101, 1709-1715: "Continuous administration of estetrol from a subcutaneous depot shows very weak uterotrophic activity and is considerably less potent than 17β-estradiol and estriol".

Tseng et al., 1976. Competition of estetrol and ethynylestradiol with estradiol for nuclear binding in human endometrium. J. Steroid Biochem. 7, 817-822: "The relative binding constant of estetrol binding to the estrogen receptor in the human endometrium is 6.25% compared to 17β-estradiol (100%)".

Martucci et al., 1976. Uterine estrogen receptor binding of catecholestrogens and of estetrol (1,3,5(10)-estratriene-3,15alpha,16alpha, 17beta-tetrol). Steroids, 27, 325-333: "Relative binding affinity of estetrol to rat uterine cytosol estrogen receptor is 0.5% of 17β-estradiol (100%). Furthermore, the relative binding affinity of estetrol to rat uterine nuclear estrogen receptor is 0.3% of 17β-estradiol (100%)".

All of the above publications have in common that the authors have investigated the estrogenic potency of estetrol. Without exception they all conclude that estetrol is a weak estrogen. In some of the cited articles the estrogenic potency of estetrol has been found to be much lower than that of the widely used and relatively weak estrogen 17β-estradiol. With these findings in mind, it is not surprising that the interest in estetrol has dwindled since the early eighties and that no publications on the properties of estetrol have been issued since.

The inventors have surprisingly found that, despite its low potency, estetrol as well as related estrogenic substances may advantageously be used in a method of treating immune mediated disorders. Although the inventors do not wish to be bound by theory, it is believed that the unexpected efficacy of the present estetrol-like substances results from the combination of the unexpected favourable pharmacodynamic and pharmacokinetic properties of these substances as well as their relatively high affinity for the estrogen receptor α (ERα) as compared to the estrogen receptor β (ERβ). The latter characteristic is an unique feature of the estrogenic substances employed in the present method.

As regards the pharmacokinetic properties of the present estrogenic substances the inventors have discovered that their in vivo half-life is considerably longer than that of other biogenic estrogens. Thus, even though estetrol and estetrol-like substances have relatively low estrogenic potency, they may effectively be employed in a method of treating immune mediated disorders because their low potency is compensated for by a relatively high metabolic stability as demonstrated by a long half-life.

The relatively high affinity of the present estrogenic substances for the ERα receptor, or conversely the relatively low affinity for the ERβ receptor, is believed to be somehow associated with the high efficacy of the present substances in the treatment of immune mediated disorders. However, as will become apparent below, the mechanisms that govern the ER signalling pathways that are responsible for this efficacy are as yet poorly understood, despite the considerable scientific effort that is ongoing in this area.

It is known that most estrogens bind to both ERs which, in the presence of tissue-specific co-activators and/or co-repressors, bind to an estrogen response element in the regulatory region of genes or to other transcription factors. Given the complexity of ER signalling, along with the tissue-specific expression of ERα and ERβ and its co-factors, it is now recognised that ER ligands can act as estrogen agonists or even as estrogen antagonists in a tissue-specific manner.

It is also known that the ERα and ERβ receptors, have significantly different amino acid sequences in the ligand binding domain and carboxy-terminal transactivation domains (about 56% amino acid identity), and only 20% homology in their amino-terminal transactivation domain. This explains why some ligands have higher affinity to one receptor over the other. In addition, interaction with co-factors may result in very different biological actions of a single ligand. In other words, a ligand that acts as an agonist on ERα is not necessarily also an agonist on ERβ and vice versa.

Furthermore it is now known that estrogen modulates cellular pharmacology through gene expression, and that the estrogen effect is mediated by the estrogen receptors. The effect of the estrogen receptor on gene regulation can be mediated by a direct binding of ER to the estrogen response element, binding of ER to other transcription factors such as NF-κB, C/EBPβ and through non-genomic effects involving ion channel receptors. Progress over the last few years has shown that ER associates with co-activators (e.g., SRC-1, CBP and SRA) and co-repressors (e.g., SMRT and N-CoR), which also modulate the transcriptional activity of ER in a tissue-specific and ligand-specific manner. In addition, evidence now suggests that the majority of estrogen-regulated genes do not have a classical estrogen response element. In such cases, ER interacts with the transcription factors critical for regulation of these genes. Transcription factors known to be modulated in their activity by ER include, for example, AP-1, NF-κB, C/EBP and Sp-1.

Given the complexity of ER signalling, as well as the various types of tissue that express ER and its co-factors, it is commonly believed that ER ligands can no longer simply be classified as either pure antagonists or agonists. This view is supported by the findings of Paech et al. (Science 277, 1508-1510, 1997) who have reported that 17β-estradiol activates an AP-1 site in the presence of ERα, but inhibits the same site in the presence of ERβ. In contrast, the ER ligands raloxifene (Eli Lilly & Co.) and tamoxifen and ICI-182,780 (Zeneca Pharmaceuticals) stimulate the AP-1 site through ERβ, but inhibit this site in the presence of ERα.

ERα and ERβ are known to have both overlapping and different tissue distributions, as analysed predominantly by RT-PCR or in-situ hybridisation. Very often tissues express both ERα and ERβ, but the receptors are localised in different cell types. In addition, some tissues (such as kidney) contain exclusively ERα, while other tissues (such as uterus, pituitary and epididymis) show a great predominance of ERα. (Couse et al., Endocrinology 138, 4613-4621, 1997; Kuiper et al., Endocrinology 138, 863-870, 1997). The development of ERα. (Korach, Science 266, 1524-1527, 1994) and ERβ (Krege et al., Proc. Natl. Acad. Sci. USA 95, 15677-82, 1998) knockout mice has produced further evidence that each of the ERs has different functions in different tissues.

In summary, although the mechanisms by which the present estrogenic substances exert their favourable effect are as yet unknown, it is evident that these substances differ from other biogenic estrogens in at least 2 relevant aspects. Firstly the present estrogenic substances exhibit an surprisingly long in vivo half-life. Secondly, the affinity of these substances for the ERα receptor in comparison to the ERβ receptor is much higher than has been observed for other (biogenic) estrogens.

Another advantageous property of the present estrogenic substances resides in the fact that sex hormone-binding globulin (SHBG) hardly binds these estrogenic substances, meaning that, in contrast to most known estrogens, serum levels are representative for bio-activity and independent of SHBG levels.

Yet another important benefit of the present estrogenic substances is derived from their relative insensitivity to interactions with other drugs (drug-drug interactions). It is well known that certain drugs may decrease the effectiveness of estrogens, such as ethinyl estradiol, and other drugs may enhance their activity, resulting in possible increased side-effects. Similarly estrogens may interfere with the metabolism of other drugs. In general, the effect of other drugs on estrogens is due to interference with the absorption, metabolism or excretion of these estrogens, whereas the effect of estrogens on other drugs is due to competition for metabolic pathways.

The clinically most significant group of estrogen-drug interactions occurs with drugs that may induce hepatic microsomal enzymes which may decrease estrogen plasma levels below therapeutic level (for example, anticonvulsant agents; phenyloin, primidone, barbiturates, carbamazepine, ethosuximide, and methosuximide; antituberculous drugs such as rifampin; antifungal drugs such as griseofulvin). The present estrogenic substances are less dependent on up- and downregulation of microsomal liver enzymes (e.g. P450's) and also are less sensitive to competition with other P450 substrates. Similarly, they do not interfere significantly in the metabolism of other drugs.

The conjugates of most estrogens, as formed in the liver, are excreted in the bile and may be broken down by gut bacteria in the colon to liberate the active hormone which can then be reabsorbed (enterohepatic recirculation). There are clinical reports that support the view that enterohepatic recirculation of estrogens decreases in women taking antibiotics such as ampicillin, tetracycline, etc. Conjugated forms of the present estrogenic substances are hardly excreted in the bile, meaning that they are substantially insensitive to drugs that do influence the enterohepatic recirculation of other estrogens.

The above observations serve to explain why the estrogenic substances of the invention hardly suffer from drug-drug interactions and thus produce a very consistent, i.e. predictable, impact.

DETAILED DESCRIPTION OF THE INVENTION

Figure 1:
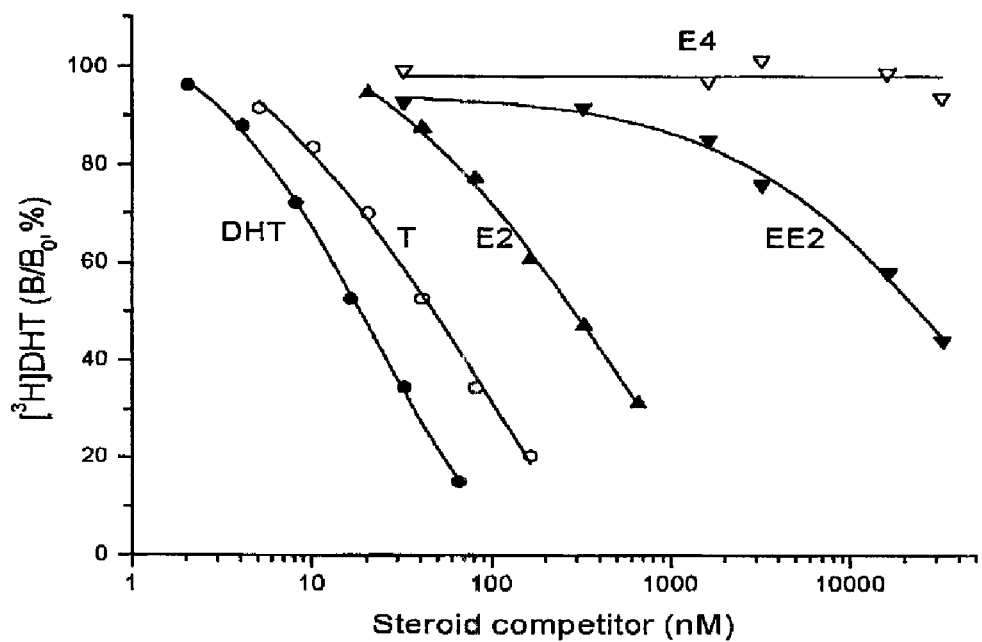
FIG. 1 shows graphs of competitive displacement of [$^3$H] DHT (panel A) and [$^3$H]estradiol (panel B) from the human sex hormone-binding globulin steroid binding site. The unlabeled steroid ligands used as competitors were as follows: estetrol (E4), 17α-ethinylestradiol (EE2), 17β-estradiol (E2), testosterone (T) and 5α-dihydrotestosterone (DHT).
Figure 1:
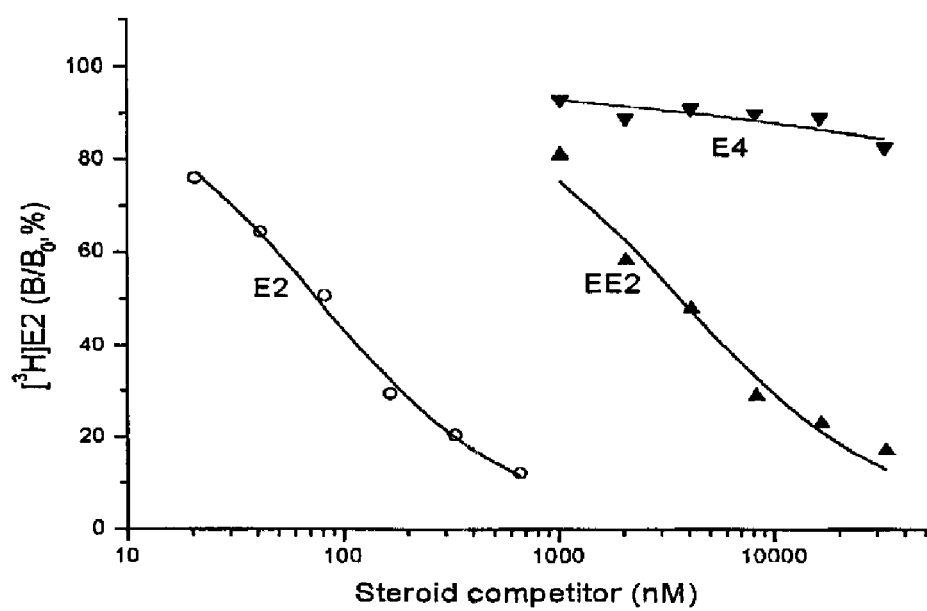

One aspect of the present invention relates to a method of treating or preventing an immune mediated disorder in a mammal, said method comprising the administration of a therapeutically effective amount of an estrogenic component to said mammal, wherein the estrogenic component is selected from the group consisting of: substances represented by the following formula

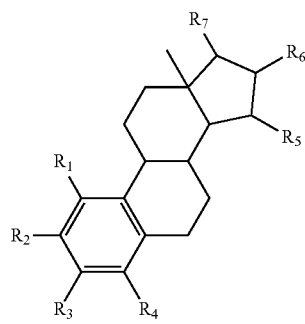

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; no more than 3 of $R_1$, $R_2$, $R_3$, $R_4$ are hydrogen atoms; precursors capable of liberating a substance according to the aforementioned formula when used in the present method; and mixtures of one or more of the aforementioned substances and/or precursors.

The present estrogen substances are distinct from both the biogenic and synthetic estrogens that are commonly applied in pharmaceutical formulations in that they contain at least 4 hydroxyl groups. The present substances are particularly special in that the 5 membered ring in the steroid skeleton comprises 3 hydroxyl substituents rather than 0-2. Examples of commercially available estrogens that contain at least 4-hydroxyl groups and their precursors are:
1,3,5(10)-estratrien-2,3,15α,16α,17β-pentol 2-methyl ether
1,3,5(10)-estratrien-2,3,15β,16α,17β-pentol 2-methyl ether
1,3,5(10)-estratrien-2,3,16α, 17β-tetrol
1,3,5(10)-estratrien-3,4,16α, 17β-tetrol 4-methyl ether
1,3,5(10)-estratrien-3,15α,16α,17β-tetrol
1,3,5(10)-estratrien-3,15α,16α,17β-tetrol tetra acetate
1,3,5(10)-estratrien-3,15β,16β,17β-tetrol tetra acetate
Preferably, the estrogenic component applied as the active component in the present composition is a so called biogenic estrogen, i.e. an estrogen that occurs naturally in the human body, a precursor of a biogenic estrogen or a mixture thereof. Because biogenic estrogens are naturally present in the fetal and female body, side-effects are not expected to occur, particularly not if the serum levels resulting from the exogenous administration of such estrogens do not substantially exceed naturally occurring concentrations. Naturally occurring estrogenic components typically exhibit a 8β, 9α, 13β, 14α configuration of the steroid-skeleton.

In a preferred embodiment of the present invention the estrogenic substance contains 4 hydroxyl groups. Also, in the aforementioned formula, $R_1$ preferably represents a hydrogen atom. In said formula preferably at least 2, more preferably at least 3 of the groups $R_1$, $R_2$, $R_3$ and $R_4$ represent a hydrogen atom.

The estrogenic substances according to the formula encompass various enantiomers since the carbon atoms that carry hydroxyl-substituents $R_5$, $R_6$ and $R_7$ are chirally active. In one preferred embodiment, the present estrogenic substance is 15α-hydroxy substituted. In another preferred embodiment the substance is 16α-hydroxy substituted. In yet another preferred embodiment, the substances is 17β-hydroxy substituted. Most preferably the estrogenic substances are 15α,16α,17β-trihydroxy substituted.

In a preferred embodiment of the present invention $R_3$ represents a hydroxyl group or an alkoxy group. In another preferred embodiment the groups $R_1$, $R_2$ and $R_4$ represent hydrogen atoms, in which case, if $R_3$, $R_5$, $R_6$ and $R_7$ are hydroxyl groups, the substance is 1,3,5 (10)-estratrien-3,15, 16,17-tetrol. A preferred isomer of the latter substance is 1,3,5 (10)-estratrien-3,15α,16α,17β-tetrol (estetrol).

The invention also encompasses the use of precursors of the estrogen substances that constitute the active component in the present method. These precursors are capable of liberating the aforementioned estrogen substances when used in the present method, e.g. as a result of metabolic conversion. These precursors are preferably selected from the group of derivatives of the present estrogen substances, wherein the hydrogen atom of at least one of the hydroxyl groups has been substituted by an acyl radical of a hydrocarbon carboxylic, sulfonic acid or sulfamic acid of 1-25 carbon atoms; tetrahydrofuranyl; tetrahydropyranyl; or a straight or branched chain glycosydic residue containing 1-20 glycosidic units per residue. Typical examples of precursors which can suitably be used in accordance with the invention are esters that can be obtained by reacting the hydroxyl groups of the estrogen substances with substances that contain one or more carboxy ($M^{+-}OOC$—) groups, wherein $M^+$ represents a hydrogen or (akali)metal cation. Hence, in a particularly preferred embodiment, the precursors are derivatives of the estrogen substances, wherein the hydrogen atom of at least one of the hydroxyl groups in said formula has been substituted by —CO—R, wherein R is a hydrocarbon radical comprising from 1-25 carbon atoms. Preferably R is hydrogen, or an alkyl, alkenyl or aryl radical comprising from 1-20 carbon atoms.

The present method is particularly effective when used in the treatment or prevention of chronic immune mediated disorders. Consequently, in a preferred embodiment, the method comprises the uninterrupted administration of the estrogenic component during a period of at least 5 days, preferably of at least 30 days.

The present method may suitably employ enteral or parenteral administration of the estrogenic component. The term "parenteral administration" as used in here encompasses transdermal, intravenous, intranasal, intravaginal, pulmonary, buccal, subcutaneous, intramuscular and intra-uterine administration. The term "enteral administration" includes oral as well as rectal administration.

Preferably the mode of administration is selected from the group consisting of oral, transdermal, intravenous, intranasal, intravaginal, pulmonary, rectal, buccal, subcutaneous, intramuscular or intra-uterine administration. More preferably the mode of administration is selected from the group consisting of oral, transdermal, intravenous, subcutaneous, intranasal, pulmonary and vaginal administration. In a particularly preferred embodiment the present method employs oral, transdermal, intranasal or subcutaneous administration. Even more preferably the present method employs oral or subcutaneous administration.

Oral, intravenous, subcutaneous, intramuscular, intranasal, rectal, buccal and pulmonary administration are ideally suited for (at least) once daily administration. Transdermal administration is advantageously applied at frequencies between once a day and once a month. Intravaginal and intra-uterine administrations are advantageously operated at administration frequencies between once weekly and once monthly. Subcutaneous and intramuscular administration may also suitably be done in the form of depot injections at intervals of 1 week to 6 months, preferably at intervals of 4 weeks to 3 months.

For reasons of convenience, the present method preferably utilises administration intervals of 1 day, 1 week or 1 month. Regimens that employ once daily oral, subcutaneous, intravenous or intranasal administration, once weekly transdermal or once monthly intravaginal or subcutaneous administration are particularly preferred.

Irrespective of the mode of administration, the estrogenic component is preferably administered in an amount effective to achieve a blood serum concentration of at least 5 nanogram per liter, more preferably of at least 50 nanogram per liter, most preferably at least 500 nanogram per liter. Generally the resulting blood serum concentration of the estrogenic component will not exceed 200 µg per liter, preferably it will not exceed 10 µg per liter, more preferably it will not exceed 50 µg per liter.

In accordance with the present method the estrogenic component is usually administered in an amount of less than 2 mg per kg of bodyweight per day, preferably of less than 0.8 mg per kg of bodyweight per day. In order to achieve a significant impact from the administration of the estrogenic component, it is advisable to administer in an amount of at least 5 µg per kg of bodyweight per day. Preferably, the administered amount is at least 25 µg per kg of bodyweight per day.

Oral administration of the active component is preferably done in an amount of less than 800 µg per kg of bodyweight per day, preferably of less than 400 µg per kg of bodyweight per day. In order to achieve a significant impact from the administration of the active component, it is advisable to orally administer in an amount of at least 10 µg per kg of bodyweight per day. Preferably, the orally administered amount is at least 25 µg per kg of bodyweight per day. In the present method, particularly when used in humans, the estrogenic component is usually administered in an average dosage of at least 0.25 mg per day, preferably of at least 0.5 mg per day. The maximum dosage is normally kept below 80 mg per day, preferably below 40 mg per day.

The present method of treatment preferably comprises administering to a person in need of such a therapy an effective amount of the estrogenic component. The amounts needed to be effective will differ from individual to individual and are determined by factors such as the individual's level of estrogen deficiency, body weight, route of administration and the efficacy of the particular estrogenic substance used.

In the present method, particularly when used in humans, the estrogenic component is usually orally administered in an average dosage of between 0.05 and 40 mg per day, preferably of between 0.25 and 20 mg per day. Similarly, parenteral dosage preferably are at least 0.25, preferably of at least 0.5 mg per day. The average maximum parenteral dosage is normally kept below 80 mg per day, preferably below 40 mg per day.

In a particularly preferred embodiment of the invention the method employs oral administration of the active estrogenic component. The term oral administration as used in here also encompasses oral gavage administration. The inventors have surprisingly found that, despite its low potency, estetrol and related estrogenic substances may advantageously be administered orally. Although the inventors do not wish to be bound by theory, it is believed that the unexpected efficacy of orally administered estetrol-like substances results from the combination of special pharmacokinetic (ADME) and pharmacodynamic properties of these substances.

The inventors have discovered that the oral bioavailability of estetrol-like substances is surprisingly high and that their in vivo half-life is considerably longer than that of commonly used biogenic estrogens. Thus, even though estetrol and estetrol-like substances have relatively low estrogenic potency, they may effectively be administered orally.

Another important advantage of oral administration of estetrol and estetrol-like substances resides in the fact that the hepatic effects of these substances are deemed to be minimal since they are hardly metabolised during the so called "first pass". The first-pass effect of drugs given orally refers to the process of drug degradation by the liver during a drug's transition from initial ingestion to circulation in the blood stream. After resorption from the intestinal lumen, orally applied active ingredients enter the organism via the liver. This fact is of specific importance for estrogenic agents as the liver is a target organ for estrogens; oral intake of estrogens results in strong estrogenic effects in the liver. Therapeutically equivalent doses of commonly used biogenic estrogens, when applied orally, result in clear responses of hepatic parameters, such as increase of SHBG, CBG, angiotensinogen and HDL (high density lipoprotein).

The present method may suitably be used in the (prophylactic) treatment of a wide variety of immune mediated disorders. The term "immune mediated disorder" as used in here, refers to any undesired immune reaction or pathology that is mediated or partially mediated by a cell of the lymphoid lineage (including T lymphocytes, B Lymphocytes) or myeloid lineage (including granulocytes, macrophages and monocytes) and which is detrimental to the mammal in which it occurs. Such undesired immune reactions or pathologies may be mediated by T lymphocytes or are multifactorial, e.g. chronic inflammatory diseases, including autoimmune diseases, immune pathologies induced by infectious agents, immune reactions by or against allografts, atopic responses, allergic reactions and immunoproliferative disorders.

The present method is particularly suitable for treating T-lymphocyte-mediated and/or chronic inflammatory diseases, including, but not limited to autoimmune diseases, such as multiple sclerosis, rheumatoid arthritis, osteoarthritis, insulin dependent diabetes (type I diabetes), systemic lupus erythrematosis and psoriasis, immune pathologies induced by infectious agents, such as helminthic (e.g., leishmaniasis) and certain viral infections, including HIV, and bacterial infections, including Lyme disease, tuberculosis and lepromatous leprosy, transplant rejection, graft versus host disease and atopic conditions, such as asthma and allergy, including allergic rhinitis, gastrointestinal allergies, including food allergies, eosinophilia, conjunctivitis and glomerular nephritis.

Many immune mediated disorders are multi-factorial, characterized by activation of multiple types of inflammatory cells, particularly cells of lymphoid lineage (including Th1 lymphocytes, Th2 lymphocytes, B-lymphocytes) and myeloid lineage (including granulocytes, macrophages, and monocytes). (Pro)inflammatory mediators, including cytokines, such as tumor necrosis factor (TNF) and interleukin-1 (IL-1), are produced by these activated cells and antibody and complement responses are common. In a particularly preferred embodiment of the invention the present method is used for treating Th1-mediated immune mediated disorders ("ml mediated disorders"). Th1 mediated disorders are pathologies in which the detrimental immune response is premarily or partially a T helper 1 (Th1) type immune response. A Th1 immune response is characterised by secretion of (pro)inflammatory cytokines such IL-12, INF-γ and TNF-α. Th1-mediated disorders include most autoimmune diseases, many alloimmune mediated disorders, certain allergic conditions, certain chronic inflammatory conditions and certain immune pathologies induced by infectious agents. An immune mediated disorder may alternatively be mediated through a Th2 immune response. In contrast to a Th1-mediated response, a Th2 mediated response is characterised by secretion of anti-inflammatory cytokines, such as IL-4, IL-10, IL-13 and TGF-β.

The present method is particularly suitable for treating or preventing immune mediated disorders selected from the group consisting of autoimmune pathologies and chronic inflammatory responses. Examples of autoimmune pathologies that can effectively be treated include multiple sclerosis (nerve cells), rheumatoid arthritis (cartilage, joint lining), osteoarthritis (cartilage), type I diabetes (pancreas), systemic lupus erythematosus (multiple tissues), psoriasis (skin), Alzheimer's disease (central nervous system), myasthenia gravis (neuromuscular junction), Crohn's disease (intestine), epididymitis (epididymis), glomerulonephritis (kidneys), Graves' disease (thyroid), Guillain-Barre syndrome (nerve cells), Hashimoto's disease (thyroid), hemolytic anemia (red blood cells), pemphigus (primarily skin), rheumatic fever (heart and joints), sarcoidosis (multiple tissues and organs), dermatomyositis (multiple tissues and organs) scleroderma (skin and connective tissues), Sjogren's syndrome (exocrine glands, and other tissues), spondyloarthropathies (axial skeleton, and other tissues), thyroiditis (thyroid), vasculitis (blood vessels), vitiligo (skin), Addison's disease (adrenal gland). Examples of chronic inflammatory responses that can suitably be treated with the present method include inflammatory responses associated with cardiovascular diseases, coronary disease, cirrhosis, arthritic diseases, cholestasis, tuberculosis, leprosy, syphilis, periodontitis, fibrosis, glomerulonephritis and certain cancers as well as chronic inflammatory responses to infectious agents such as bacteria, viruses, fungi, protozoa, helminths and prions.

The method of the invention is deemed to be particularly suitable for the treatment of immune mediated disorders resulting in neurological pathologies, e.g multiple sclerosis, Alzheimers disease, myesthenia gravis, Guillain-Barre syndrome, amyotrophic lateral sclerosis.

The present method is also deemed to be very suitable for the treatment of immune mediated disorders resulting in muscleskeletal pathologies, e.g. rheumatoid arthritis, osteoarthritis, and related inflammatory arthritic diseases, comprising gout, spondylarthropathris, ankylosing spondylitis, Reiter's syndrome, psoriatic arthropathy, enterapathric spondylitis, juvenile arthropathy or juvenile ankylosing spondylitis, reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis, carpal tunnel syndrome, repetitive use injury, miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, such as surcoilosis, hemochromatosis, sickle cell disease and other hemoglobinopathries, hyperlipoproteinemia, hypogammaglobulinemia, hyperparathyroidism, acromegaly, familial Mediterranean fever, Behat's Disease, systemic lupus erythrematosis, or relapsing polychondritis.

The method of the invention is deemed to be particularly advantageous when it is used in the (prophylactic) treatment of an immune mediated disorder selected from the group consisting of multiple sclerosis, rheumatoid arthritis, osteoarthritis, insulin dependent diabetes (type I diabetes), systemic lupus erythrematosis and psoriasis. Most advantageously the present method is employed in the treatment of multiple sclerosis, rheumatoid arthritis or osteoarthritis.

In order to reinforce the action of the estrogenic component it may be advantageous to co-administer an immunotherapeutic agent, that is capable of prophylactically or therapeutically inhibiting an immune response and/or of ameliorating immune pathology. Such agents are known in the art and comprise immunosuppressive, immunomodulatory, immunoblocking and/or anti-inflammatory agents and may be administered in combination with the estrogenic component, i.e. in a single unit dosage form, or alternatively these active principles may be administered separately, especially if the modes of administration are different.

In a specific embodiment, the estrogenic component of the present invention is administered in combination with one or more immunotherapeutic drugs to a mammal having or being susceptible to multiple sclerosis. Administration of the estrogenic component of the present invention in combination with one or more immunotherapeutic drugs may enhance the effectiveness of the treatment. In addition, such a combination may generate fewer or less pronounced side effects, and/or can make it possible to administer a lower dose of the known immunotherapeutic drug or estrogenic component to produce the same effect as a substantially higher dose of either component alone. The immunotherapeutic drug for use in the treatment of multiple sclerosis can suitably be: (1) a steroidal anti-inflammatory agent, such as cortisol or dexamethasone (2) nonsteroidal anti-inflammatory agent such acetylsalicylic (aspirin), ibuprofen, or naproxen; (3) D-pencillamine; (4) a 4-aminoquinoline agent such as hydroxychloroquine; (5) azathioprine; (6) methotrexate; (7) cyclosporin; (8) monoclonal antibodies to T lymphocytes; (9) monoclonal antibodies to adhesion molecules; (10) monoclonal antibodies to cytokines and growth factors; (11) Tumor Necrosis Factor Receptor (TNFR)-IgG; (12) IL-1 receptor antagonists; (13) ICE inhibitors, (14) betaferon and/or (15) vitamin D, 1α,25-dihydroxyvitamin $D_3$ and 1α,25-dihydroxyvitamin $D_2$, (16) agents that specifically bind a molecule selected from the group consisting of a T cell receptor, an antigen and a HLA molecule.

In another specific embodiment, the estrogenic component of the present invention is administered in combination with one or more immunotherapeutic drugs to a mammal having or being susceptible to rheumatoid arthritis. Administration of the estrogenic component of the present invention in combination with one or more immunotherapeutic drugs may enhance the effectiveness of the treatment of arthritic diseases such as rheumatoid arthritis and osteoarthritis. In addition, such a combination may provide less side effects, and/or enable administration of a lower dose of the immunotherapeutic drug or estrogenic component whilst producing the same effect as a substantially higher dose of either component alone. The immunotherapeutic drug for use in the treatment of rheumatoid arthritis can be: (1) a steroidal anti-inflammatory agent, such as cortisol or dexamethasone (2) nonsteroidal anti-inflammatory agent such acetylsalicylic (aspirin), ibuprofen, or naproxen; (3) an organic gold derivative such a gold sodium thiomalate, aurothioglucose, or auranofin; (4) D-pencillamine; (5) a 4-aminoquinoline agent such as hydroxychloroquine; (6) azathioprine; (7) methotrexate; (8) cyclosporin; (9) an angiogenesis inhibitor such as AGM-1470 (Ingber, et al., 1990, Nature 348, 555); (10) monoclonal antibodies to T lymphocytes; (11) monoclonal antibodies to adhesion molecules; (12) monoclonal antibodies to cytokines and growth factors; (13) Tumor Necrosis Factor Receptor (TNFR)-IgG; (14) IL-1 receptor antagonists; (15) ICE inhibitors, and/or (16) agents that specifically bind a molecule selected from the group consisting of a T cell receptor, an antigen and a HLA molecule.

In another preferred embodiment of the invention the present method comprises the co-administration of a progestogen, particularly if the method is employed in the treatment of female mammals. The administration of estrogens has been associated with endometrial proliferation in women and it is now widely accepted that "unopposed" estrogen administration during a prolonged period of time (estrogen therapy) substantially increases the risk of endometrial cancer (Cushing et al., 1998. Obstet. Gynecol. 91, 35-39; Tavani et al., 1999. Drugs Aging, 14, 347-357). There is also evidence of a significant increase in breast cancer with long-term (10-15 years) use of estrogen therapy (Tavani et al., 1999. Drugs Aging, 14, 347-357; Pike et al., 2000. Steroids, 65, 659-664).

In order to counteract the negative effects of prolonged unopposed estrogen therapy, adjunctive progestogen treatment is nowadays commonly applied in hormone replacement therapy in peri- and postmenopausal women. Regular progestogen administration is believed to inhibit the continual estrogen stimulation of the endometrium through an anti-proliferative effect and appears to reduce the incidence of endometrial carcinoma in post-menopausal women receiving estrogen replacement therapy (Beral et al., 1999. J. Epidemiol. Biostat., 4, 191-210). In order to counteract any potential negative effects of unopposed estrogen administration in the present method, particularly in case of prolonged continuous administration, it is preferred to co-administer a progestogenic component to inhibit estrogen stimulation of the endometrium or to administer a progestogenic component at least during a period of ten days at least every three months.

Another aspect of the invention relates to a pharmaceutical formulation comprising the estrogenic component and the immunotherapeutic agent as defined herein before, and a pharmaceutically acceptable excipient. The present pharmaceutical formulation preferably contains at least 10 μg of the estrogenic component, more preferably at least 25 μg of said estrogenic component. Even more preferably the amount of the estrogenic component within the formulation is at least 50 most preferably it will be at least 150 μg. The amount of the estrogenic component within the formulation will normally not exceed 1000 mg. Preferably the amount will not exceed 600 mg, most preferably it will not exceed 400 mg.

The immunotherapeutic agent is suitable present in the formulation in an amount of at least 1 μg, preferably at least 10 μg. Usually the amount of the immunotherapeutic agent within the formulation will not exceed 50 mg, preferably it will not exceed 25 mg.

The pharmaceutical formulation according to the invention can suitably be a solid or semi-solid dosage form such as tablets, capsules, cachets, pellets, pills, powders and granules, as well as fluid dosage forms such as solutions, emulsions, suspensions, ointments, pastes, creams, gels, jellies and foams.

The oral dosage unit according to the invention is preferably a solid or semi-solid dosage form such as tablets, capsules, cachets, pellets, pills, powders and granules. The term "solid or semi-solid dosage form" also encompasses capsules that contain a liquid, e.g. an oil, in which the present estrogenic component is dissolved or dispersed. Tablets and equivalent solid and semi-solid dosage forms can suitably contain materials such as binders (e.g. hydroxypropylmethyl cellulose, polyvinyl pyrrolidine, other cellulosic materials and starch), diluents (e.g. lactose and other sugars, starch, dicalcium phosphate and cellulosic materials), disintegrating agents (e.g. starch polymers and cellulosic materials) and lubricating agents (e.g., stearates and talc).

Transdermal delivery systems include patches, gels, tapes and creams, and can contain excipients such as solubilisers, permeation enhancers (e.g. fatty acids, fatty acid esters, fatty alcohols and amino acids), hydrophilic polymers (e.g. polycarbophil and polyvinyl pyrrolidine) and adhesives and tackifiers (e.g. polyisobutylenes, silicone-based adhesives, acrylates and polybutene).

Transmucosal (notably rectal and intravaginal) delivery systems include patches, tablets, suppositories, pessaries, gels, and creams, and can contain excipients such as solubilizers and enhancers (e.g. propylene glycol, bile salts and amino acids), and other vehicles (e.g. polyethylene glycol, fatty acid esters and derivatives, and hydrophilic polymers such as hydroxypropylmethyl cellulose and hyaluronic acid).

Injectable or implantable depot preparations include injectable fluids and implantation tablets. Suitable fluid carrier components are physiologically compatible diluents wherein the active agents can be dissolved, suspended. An example of a diluent is water, with or without addition of electrolyte salts or thickeners. Thus, the depot formulation can be, for example, an aqueous microcrystalline suspension. Oils are particularly suitable as diluents, with or without the addition of a solubiliser, of a surfactant, or of a suspension or emulsifying agent. Examples of suitable oils include arachidis oil, olive oil, peanut oil, cottonseed oil, soybean oil, castor oil, and sesame oil. Examples of solubilisers include benzyl alcohol and benzyl benzoate. Depot preparations offer the advantage that a single injection or implantation suffices for one or several months. Duration of the depot effect depends the nature of the estrogenic component (the ester precursors being preferred as they display a slower release), the amount of the estrogenic component as well as on the type of carrier substance that releases the active agent. Generally, the duration will be in the range of 10-30 days, but longer or shorter times can also be achieved.

Other delivery systems that can be used for administering the pharmaceutical composition of the invention include intranasal and pulmonary delivery systems such as sprays and microparticles.

Another, particularly preferred aspect of the present invention relates to an oral unit dosage form comprising at least 50 μg, preferably at least 250 μg of the estrogenic component and at least 1 μg of an immunotherapeutic agent as defined herein before, and a pharmaceutically acceptable excipient.

The present invention is further illustrated by the following examples, which, however, are not to be construed as limiting. The features disclosed in the foregoing description, in the following examples and in the claims may, both separately and in any combination thereof, be material for realising the invention in diverse forms thereof.

EXAMPLES

Example 1

Vaginal cornification was chosen as a tissue-specific and estrogen-sensitive endpoint to determine the estrogenicity of estetrol (E4), after both oral and subcutaneous administration, in hypoestrogenic rats. 17α-ethinylestradiol (EE), 17β-estradiol (E2) and vehicle (10% ethanol/sesame oil) served as controls in these bioassays.

Uterine weight increase in the rat is more commonly used as a measure of estrogenicity. However, uterine weight also responds to progesterone, testosterone, and other agents not characteristically regarded as estrogens. In the early 1920s it was discovered that follicular fluid from the pig ovary contained a factor(s) that caused cornification/keratinization of the vaginal epithelium in the rat (Allen and Doisy, 1923, JAMA, 81, 819-821; Allen and Doisy, 1924, Am. J. Physiol., 69, 577-588). The so-called vaginal cornification response in rats subsequently provided a bioassay for testing estrogenicity. Vaginal epithelial cornification/keratinization in ovariectomized rats can be produced only by compounds considered to be true estrogens (Jones et al, 1973, Fert. Steril. 24, 284-291). Vaginal epithelial cornification/keratinization represents, therefore, a highly selective endpoint to determine the potency of estrogens (Reel et al., 1996, Fund. Appli. Toxicol. 34, 288-305).

Adult intact female CD rats were ovariectomized to induce estrogen deficiency. Vaginal lavages were performed daily for seven days to ensure that the rats demonstrated castrate vaginal smears (predominance of leukocytes in the vaginal smear, and similar in appearance to a diestrous vaginal smear). Castrate vaginal smears are indicative that complete ovariectomy was achieved. Treatment commenced following completion of the 7 days of smearing (day 0=first day of dosing). Animals were dosed, once daily for 7 consecutive days. Daily vaginal lavages continued to be obtained for 7 days after dosing was initiated in order to detect vaginal cornification, as an indication of an estrogenic response. A drop of vaginal washings was placed on a glass slide and examined by light microscopy to detect the presence or absence of cornified epithelial cells. Vaginal lavages were obtained prior to dosing on days 0-6 and prior to necropsy on day 7.

The vaginal cornification bioassay was performed in order to determine the estrogenic profile of E4 when given subcutaneously (sc) to ovariectomized adult rats. E2 was used as a positive control. The vehicle (10% ethanol/sesame oil) served as the negative control. Steroids were dissolved in absolute ethanol and then brought to the final concentration with sesame oil (10% ethanol in sesame oil). A vaginal estrogenic response occurred in 8/8 rats by day 2 and persisted through day 7 in rats injected sc with 50 μg/kg/day E2 for 7 days (Table 1). Animals treated with the vehicle did not exhibit vaginal epithelial cornification (Table 1). The onset of vaginal epithelial cornification was dose-dependent in rats injected sc with 0.1, 0.3, 1.0, and 3.0 mg/kg/day E4 and started at the same day of treatment (Day 2) as observed for E2 (Table 1). At 0.1 mg/kg/day E4 already 4/8 rats and at 0.3 mg/kg/day E4 even 7/8 rats exhibited a vaginal estrogenic response by day 7. At 1.0 and 3.0 mg/kg/day E4 all rats showed a vaginal estrogenic response by day 7 (Table 1).

TABLE 1

Vaginal estrogenic response in ovariectomized rats treated subcutaneously (sc) with 17β-estradiol (E2) or estetrol (E4). Data are expressed as the number of rats showing vaginal cornification over the number of rats (ratio) treated.

| Treatment Group | Dosing route | Number of Rats Exhibiting Estrogenic Response/ Number of Rats Treated Day of Study | | | | | | | |
|---|---|---|---|---|---|---|---|---|---|
| | | Day 0 | Day 1 | Day 2 | Day 3 | Day 4 | Day 5 | Day 6 | Day 7 |
| 0.05 mg/kg/day E2 | sc | 0/8 | 0/8 | 8/8 | 8/8 | 8/8 | 8/8 | 8/8 | 8/8 |
| Vehicle Control | sc | 0/8 | 0/8 | 0/8 | 0/8 | 0/8 | 0/8 | 0/8 | 0/8 |
| 0.1 mg/kg/day E4 | sc | 0/8 | 0/8 | 0/8 | 1/8 | 1/8 | 4/8 | 3/8 | 4/8 |
| 0.3 mg/kg/day E4 | sc | 0/8 | 0/8 | 1/8 | 5/8 | 7/8 | 6/8 | 7/8 | 7/8 |
| 1.0 mg/kg/day E4 | sc | 0/8 | 0/8 | 1/8 | 6/8 | 8/8 | 7/8 | 8/8 | 8/8 |
| 3.0 mg/kg/day E4 | sc | 0/8 | 0/8 | 3/8 | 8/8 | 8/8 | 8/8 | 8/8 | 8/8 |

The vaginal cornification bioassay was performed in order to determine the estrogenic profile of E4 when given orally (po) to ovariectomized adult rats. EE was used as a positive control. The vehicle (10% ethanol/sesame oil) served as the negative control. Steroids were dissolved in absolute ethanol and then brought to the final concentration with sesame oil (10% ethanol in sesame oil). A vaginal estrogenic response occurred in all rats (8/8) given 50 μg/kg/day EE po by day 7 (Table 2). Similarly, vaginal epithelial cornification was observed in all rats (8/8) treated po with either 0.1, 0.3, 1.0, or 3.0 mg/kg/day E4 by day 7 (Table 2), whereas animals treated with the vehicle did not exhibit vaginal epithelial cornification (0/8). Surprisingly, even in rats given relatively low doses of E4 (e.g. 0.1 mg/kg/day), the onset of vaginal cornification (defined as the amount of animals responding at days 1-3 of the study) was faster in po-treated than in sc-treated animals, demonstrating estetrol's superb bioavailability characteristics after oral administration.

TABLE 2

Vaginal estrogenic response in ovariectomized rats treated orally (po) with 17α-ethinyl estradiol (EE) or estetrol (E4). Data are expressed as the number of rats showing vaginal cornification over the number of rats (ratio) treated.

| Treatment Group | Dosing route | Number of Rats Exhibiting Estrogenic Response/Number of Rats Treated Day of Study | | | | | | | |
|---|---|---|---|---|---|---|---|---|---|
| | | Day 0 | Day 1 | Day 2 | Day 3 | Day 4 | Day 5 | Day 6 | Day 7 |
| 0.05 mg/kg/day EE | po | 0/8 | 1/8 | 3/8 | 8/8 | 8/8 | 8/8 | 8/8 | 8/8 |
| Vehicle Control (2 ml/kg/day) | po | 0/8 | 0/8 | 0/8 | 0/8 | 0/8 | 0/8 | 0/8 | 0/8 |
| 0.1 mg/kg/day E4 | po | 0/8 | 0/8 | 1/8 | 7/8 | 8/8 | 8/8 | 8/8 | 8/8 |
| 0.3 mg/kg/day E4 | po | 0/8 | 0/8 | 1/8 | 7/8 | 8/8 | 8/8 | 8/8 | 8/8 |
| 1.0 mg/kg/day E4 | po | 0/8 | 0/8 | 4/8 | 8/8 | 8/8 | 8/8 | 8/8 | 8/8 |
| 3.0 mg/kg/day E4 | po | 0/8 | 0/8 | 6/8 | 8/8 | 8/8 | 8/8 | 8/8 | 8/8 |

Example 2

To evaluate the oral (po) and subcutaneous (sc) bioavailability of estetrol (E4) and to determine the elimination half-life, single dose studies were performed in female Sprague Dawley rats followed by frequent blood sampling over a 24 hours interval.

Female Sprague Dawley rats were equipped with a permanent silatic heart catheter, as described by Kuipers et al. (1985, Gastroenterology, 88, 403-411). Rats were allowed to recover from surgery for 5 days and were than administered 0.05, 0.5, or 5 mg/kg E4 in 0.5 ml arachidis oil. For sc administration, E4 was injected in the neck area using a 1 ml syringe and 20 g needle. For po administration of E4, rats were lightly anaesthesized with halothene/$N_2O/O_2$ and E4 was directly applied intragastrically using a plastic stomach intubator. Blood samples were subsequently collected via the heart catheter in heparinized tubes at 0.5, 1, 2, 4, 8 and 24 hours. Erythrocytes were removed by centrifugation at 5000×g for 10 minutes at 4° C. and blood plasma was stored at −20° C. After thawing the plasma samples, liquid-liquid extraction (hexane and diethyl ether) was employed to prepare the E4-containing plasma samples for HPLC analysis (Perkin Elmer 200) and tandem mass spectrometry using a PE Sciex 3000 tandem mass spectrometer and APCI interface. With each sample batch, a calibration curve with 6 calibrators was recorded. The calibration curve was calculated using linear regression (correlation coefficient >0.98), which permitted quantitation of plasma concentrations. For each rat plasma, sampled at different time intervals, data were collected.

Plasma E4 concentration data were analysed with "WinNonLin, edition 3.1" and involved pharmacokinetic parameters for $C_{max}$, half-life and $AUC_{0-24}$. Especially, using the lower and intermediate dose levels of 0.05, 0.5 mg/kg, E4 demonstrated an oral bioavailability equal to the bioavailability obtained with sc administration (80-100%). At the highest dose level tested, 5.0 mg/kg E4, absorption kinetics gave rise to an oral bioavailability approximating 30-60% of sc administered E4. Interestingly, E4 demonstrated a relatively long half-life of 2-3 hours, enabling the detection of bioactive levels of unconjugated E4 at all time points over a 24 hour interval in the sc and po dosing experiments.

Example 3

To determine the bioavailability and elimination half-life of estetrol after oral dosing in humans a single rising dosing study was performed in healthy postmenopausal volunteers. Volunteers (n=6) were randomly assigned to 0.1, 1 or 10 mg estetrol and blood samples (18 per volunteer) were obtained over a period of 72 hours.

After thawing the plasma samples, liquid-liquid extraction (hexane and diethyl ether) was employed to prepare the estetrol-containing plasma samples for HPLC analysis (Perkin Elmer 200) and tandem mass spectrometry using a PE Sciex 4000 tandem mass spectrometer and APCI interface. With each sample batch, a calibration curve with 6 calibrators was recorded. The calibration curve was calculated using linear regression (correlation coefficient >0.98), which permitted quantitation of plasma concentrations.

Good tolerability was observed when increasing the oral estetrol dose from 0.1 to 1 and further to 10 mg. AUC values demonstrated good dose-linearity, indicating that, over the entire dose range, orally administered estetrol was well absorbed. Interestingly, estetrol demonstrated a long elimination half-life of more than 15 hours, i.e. 15-50 hours in human postmenopausal subjects.

Example 4

Established competitive steroid binding assays were used to determine the relative binding affinity of estetrol (E4), as compared to 17α-ethinylestradiol (EE) and 17β-estradiol (E2), to human Estrogen Receptor (ER) α- and β-forms.

The method employed was adapted from the scientific literature and described in detail by Osbourn et al. (1993, Biochemistry, 32, 6229-6236). Recombinant human ERα and ERβ proteins were purified from transfected Sf9-cells. The in vitro assays involved the use of either ERα or ERβ proteins and [$^3$H]E2, at a fixed concentration of 0.5 nM, as the labeled ligand. Recombinant human ERα or ERGS proteins were dissolved in binding buffer (10 mM Tris-HCL, pH 7.5, 10% glycerol, 1 mM DTT, 1 mg/ml BSA) and duplicate aliquots were then incubated with [$^3$H]E2 at a final concentration of 0.5 nM, together with a vehicle control (0.4% DMSO), or the same amount of vehicle containing increasing concentrations of unlabeled steroid ligands as competitors.

After incubation for 2 h at 25° C., the unbound ligands were removed and the amounts of [$^3$H]E2 bound to either ERα or ERβ proteins were measured. The average amounts of [$^3$H]E2 bound to either ERα or ERβ proteins at each concentration of competitor were used to make inhibition curves. IC50 values were subsequently determined by a non-linear, least squares regression analysis. Inhibition constants (Ki) were calculated using the equation of Cheng and Prusoff (Cheng et al., 1973, Biochem. Pharmacol., 22, 3099-3108), using the measured 1050 of the tested compounds, the concentration of radioligand employed in the assay, and the historical values for the Kd of the radioligand, which were established as 0.2 nM and 0.13 nM for ERα and ERβ, respectively.

Biochemical assay results for E4 are presented as the percent inhibition of specific binding in three separate experiments (Table 3). For comparision of binding affinities of E4, EE and E2 to human ERα and ERβ proteins, experimentally observed Ki values are shown in Table 4. As compared to EE and E2, E4 demonstrates a unique binding profile with a strong preference (400%) for binding to the ERα protein (Table 4). In contrast, Ki values for ERβ protein are more pronounced for EE and E2 steroid ligands (Table 4).

TABLE 3

Percent inhibition of specific binding to ERα and ERβ proteins using E4 as unlabeled steroid ligand and 0.5 nM [3H] as labeled competitor. Results of three separate experiments are shown.

| E4 final concentration | Percent inhibition of specific binding in | | | | | |
| --- | --- | --- | --- | --- | --- | --- |
| | ERα steroid binding assay | | | ERβ steroid binding assay | | |
| | Test 1 | Test 2 | Test 3 | Test 1 | Test 2 | Test 3 |
| 1 µM | 98 | nd | nd | 87 | 90 | 95 |
| 0.3 µM | 92 | 94 | 101 | 74 | 74 | 77 |
| 0.1 µM | 83 | 85 | 86 | 56 | 54 | 50 |
| 0.03 µM | 64 | 66 | 63 | 19 | 25 | 30 |
| 10 nM | 43 | 32 | 28 | nd | nd | nd |
| 3 nM | 26 | 17 | 11 | nd | nd | nd | nd: not determined

TABLE 4

Experimentally determined inhibition constants (Ki) for estetrol (E4), 17α-ethinylestradiol (EE) and l7β-estradiol (E2), to human ERα and ERβ proteins. Relative preference for binding to ERα protein is also shown.

| Steroid ligands | Ki ERα (nM) | Ki ERβ (nM) | Relative ERα/ERβ preference (%) |
| --- | --- | --- | --- |
| EE | 0.23 | 0.025 | 11 |
| E2 | 0.21 | 0.015 | 7 |
| E4 | 4.9 | 19 | 400 |

Example 5

An established competitive steroid-binding assay (Hammond and Lahteenmaki. 1983. Clin Chem Acta 132:101-110) was used to determine the relative binding affinity of estetrol (E4), 17α-ethinylestradiolEE2), 17β-estradiol (E2), testosterone (T) and 5α-dihydrotestosterone (DHT) for human sex Hormone Binding Globulin (SHBG).

Human SHBG was purified from transgenic mouse serum, as described previously (Avvakumov G V et al., 2000. J Biol Chem 275: 25920-25925). The human SHBG prepared in this way was assessed to be >99% pure by polyacrylamide gel electrophoresis under denaturing conditions. Its steroid-binding characteristics are indistinguishable from SHBG in human serum (Avvakumov G V et al., 2000. J Biol Chem 275: 25920-25925). The in vitro assay involved the use of the purified human SHBG and [$^3$H]DHT or [$^3$H]estradiol as labeled ligands. Human SHBG was treated for 30 min at room temperature with a dextran-coated charcoal (DCC) suspension in phosphate buffered saline (PBS) to remove any steroid ligand. After centrifugation (2,000×g for 10 min) to sediment the DCC, the supernatant containing the human SHBG was diluted in PBS to a concentration of 1 nM based on its steroid binding capacity.

Duplicate aliquots (100 µl) of this human SHBG solution were then incubated with an equal volume of either [$^3$H]DHT or [$^3$H]estradiol at 10 nM, together with 100 µl of PBS alone or the same amount of PBS containing increasing concentrations of unlabeled steroid ligands as competitors in polystyrene test tubes. After incubation for 1 h at room temperature the reaction mixtures were placed in an ice bath for a further 15 min. Aliquots (600 µl) of an ice cold suspension of DCC were then added to each tube, and after a brief 2 seconds mixing, each tube was incubated in an ice bath for either 10 min or 5 min depending on whether [$^3$H]DHT or [$^3$H]estradiol were being used as labeled ligands, respectively. The unbound ligands adsorbed to DCC were then removed by centrifugation (2, 000×g for 15 min at 4 C), and the amounts of [$^3$H]labeled ligands bound to SHBG were counted in 2 ml ACS scintillation cocktail using in liquid scintillation spectrophotometer. The average amounts of [$^3$H]labeled ligands bound to SHBG at each concentration of competitor (B) were expressed as a percentage of the average amounts of [$^3$H] labeled ligands bound to SHBG in the absence of competitor ($B_0$), and were plotted against the concentration of competitor in each assay tube. The results of the competitive binding assays are depicted in FIG. 1.

As is clearly apparent from these competitive binding assays, estetrol does not bind at all to human SHBG when tested with either [$^3$H]DHT or [$^3$H]estradiol as labeled ligands. This is in marked contrast with reference steroids ethinylestradiol, 17β-estradiol, testosterone and 5α-dihydrotestosterone, which, in this order, show an increased relative binding affinity for human SHBG. Importantly, estetrol binding to SHBG was negligible when compared with the other estrogens tested, ethinylestradiol and 17β-estradiol.

Example 6

Experimental autoimmune encephalomyelitis (EAE) is widely used as an animal model for Multiple Sclerosis (MS), a disease characterized by inflammatory processes within the central nervous system. Apart from its value to identify therapeutics for multiple sclerosis it is useful as a model of inflammation in general. The advantage is that the inflammatory response is localized within the central nervous system, which allows a proper appreciation of the magnitude of the inflammatory reaction in relation to clinical symptoms. Moreover, the induction of disease is precisely controlled because it is established by immunization with a protein or a synthetic peptide. Clinical monitoring of the animals is required for a period not longer than 4 to 6 weeks and fast screening of potential anti-inflammatory compounds is therefore possible.

Multiple Sclerosis is characterized by increasing disability due to disruption of the axon-surrounding myelin sheath and subsequent loss of nerve conductivity. Inflammatory lesions show an involvement of lymphocytes and macrophages that are responsible for tissue destruction via the secretion of a variety of inflammatory mediators.

EAE can be established in susceptible animal strains by immunization with whole myelin or myelin-derived proteins and peptides. In the SJL/J mouse EAE can reproducibly be induced by subcutaneous immunization with a peptide from proteolipid protein, i.e. $PLP_{139-151}$, in Freund's complete adjuvant. After 3 days, mice receive $10^9$ heat-killed *Bordetella pertussis* organisms (i.v.) to increase the permeability of the blood-brain-barrier. This results in the activation of antigen-specific T cells secreting pro-inflammatory cytokines such as lymphotoxin and interferon-γ. Development of disease is known to comprise the following events:

1. Activation of T cells by macrophages and dendritic cells that present $PLP_{139-151}$.
2. Elevated expression of interleukin-12 in macrophages and dendritic cells.
3. Differentiation of T cells into effector cells that secrete pro-inflammatory cells and express unique chemokine receptors.
4. Increased permeability of the blood-brain-barrier
5. Migration of effector cells and monocytes into brain parenchyma against a gradient of chemokines.
6. Local (re-)activation of inflammatory cells.
7. Release of mediators of inflammation and destruction of oligodendrocytes and myelin.

Typically, between 70 to 90% of vehicle-treated SJL/J mice develop a first episode of disease between days 10 and 20 post-immunization with $PLP_{139-151}$. Interestingly, about 50% of the affected animals also develop a second EAE episode (relapse) between days 28 and 42.

The effect of oral treatment with estetrol on EAE was evaluated in a 42-day study design using clinical severity of EAE (disability score) as the outcome parameter. The clinical scoring system which has been developed by Kono et al. (J Exp Med 168, 213-227, 1988) was used to monitor the degree of disability in the SJL/J EAE model: 0: no disease; 0.5: tail paresis or partial paralysis; 1: complete tail paralysis; 2: paraparesis, limb weakness and tail paralysis; 2.5: partial limb paralysis; 3: complete hind- or front limb paralysis; 3.5: paraplegia; 4: quadriplegia, moribund; 5: death due to EAE. Groups consisting of 9 to 10 female SJL/J mice were treated once daily orally with four different dosages of estetrol of 3 mg/kg, 1 mg/kg, 0.3 mg/kg and 0.1 mg/kg after disease induction by subcutaneous immunization with $PLP_{139-151}$ and continuing for the entire monitoring period of 42 days. A group treated with vehicle (Cavasol; Hydroxypropyl-beta-cyclodextrin) served as a negative control.

Female SJL/J mice at 7 weeks of age were obtained from Harlan (France). Before the start of the study, mice were handled and acclimatized for a period of two weeks and randomized over the treatment groups. Mice were immunized by subcutaneous injection of 50 μg of a synthetic peptide from proteolipid protein, i.e. $PLP_{139-151}$ (Isogen Bioscience B.V.), emulsified in Complete Freund's Adjuvant (CFA, H37Ra Lot. 2116643, Difco Laboratories, USA). The emulsion was distributed over 4 sites in the flanks. On day 3 mice received an intravenous injection of $10^9$ *Bordetella pertussis* bacteria (National Institute for Public Health, Bilthoven, The Netherlands). From day 0 (after $PLP_{139-151}$ immunization) onwards to day 42, mice were orally treated (per gavage) with 0.2 ml of estetrol solution or vehicle (hydroxypropyl-beta-cyclodextrin in a 20% wt/vol solution in water) according to the following schedule: Group A: vehicle (n=10); Group B: estetrol, 3 mg/kg/day (n=9); Group C: estetrol, 1 mg/kg/day (n=10); Group D: estetrol, 0.3 mg/kg/day (n=10) and Group E: estetrol, 0.1 mg/kg/day (n=10). When needed, dosing was adjusted to the weight of the animals which was determined daily. For individual mice, EAE disability scoring was performed daily. At the end of the treatment and monitoring period mice were sacrificed.

Statistical analyses were performed by analysis of variance (ANOVA) to test the significance of differences between treatment groups and vehicle group in the disability outcome parameters. Each parameter that showed a significant difference by ANOVA was subsequently tested by a post-hoc LSD (Least Significant Difference) test to determine which groups were different (P≦0.05 indicated statistically significant differences; P>0.05 was considered not significant). All statistical analyses were performed using a statistical software program SPSS 11.0 for Windows (SPSS Inc., Chicago, Ill., USA).

Figure 2:
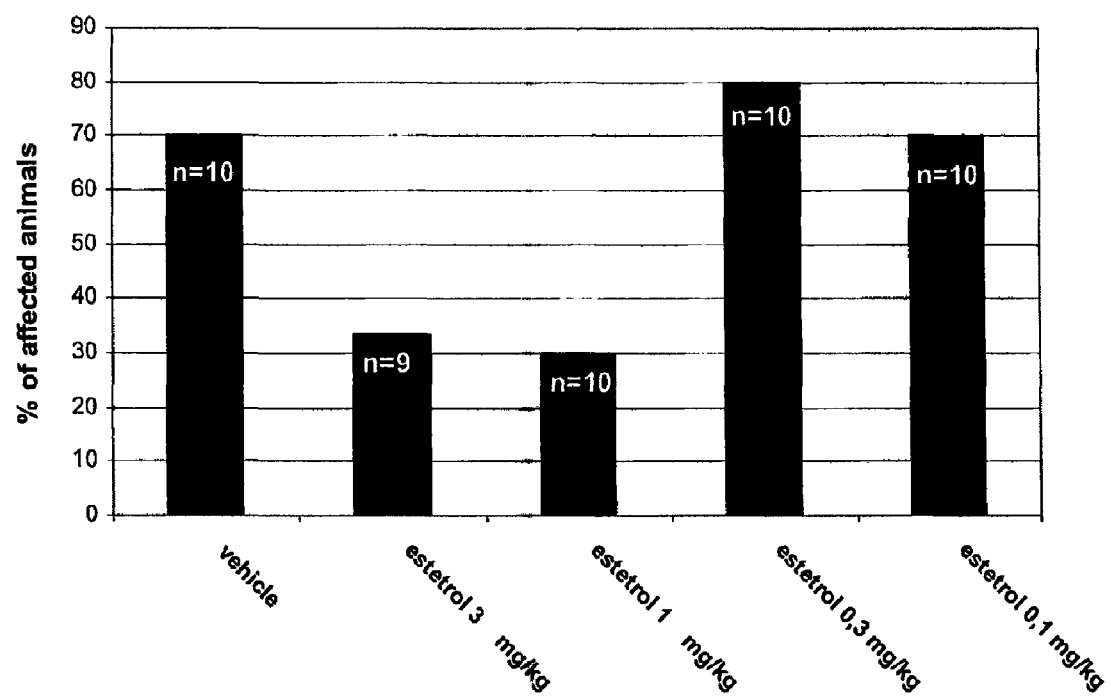
FIG. 2 is a graph showing the effect of treatment with estetrol on the incidence of EAE in SJL/J mice.

No clinical symptoms other than those related to EAE were observed in the study, indicating that estetrol did not induce any significant side-effects. Mice were considered to be affected by EAE when a cumulative score of at least 3 was reached within a period of three consecutive days. Accordingly, 70% of the vehicle treated mice developed EAE (FIG. 2). Treatment with estetrol 3 mg/kg and 1 mg/kg suppressed EAE incidence and resulted in EAE in 40% and 33% of mice, respectively (FIG. 2). Of the mice treated with estetrol 0.3 and 0.1 mg/kg 80% and 70% developed EAE, respectively.

Clinical EAE symptoms became apparent at day 12 after immunization in vehicle-treated mice. Of the mice treated with the highest dosages of estetrol (3 and 1 mg/kg) the mean day of onset was delayed to 15.7 and 14.7 days, respectively. Treatment with the two lowest dosages estetrol (0.3 and 0.1 mg/kg) also showed a trend of delayed disease onset as compared to vehicle-treated mice, but this was not statistically significant.

Figure 3:
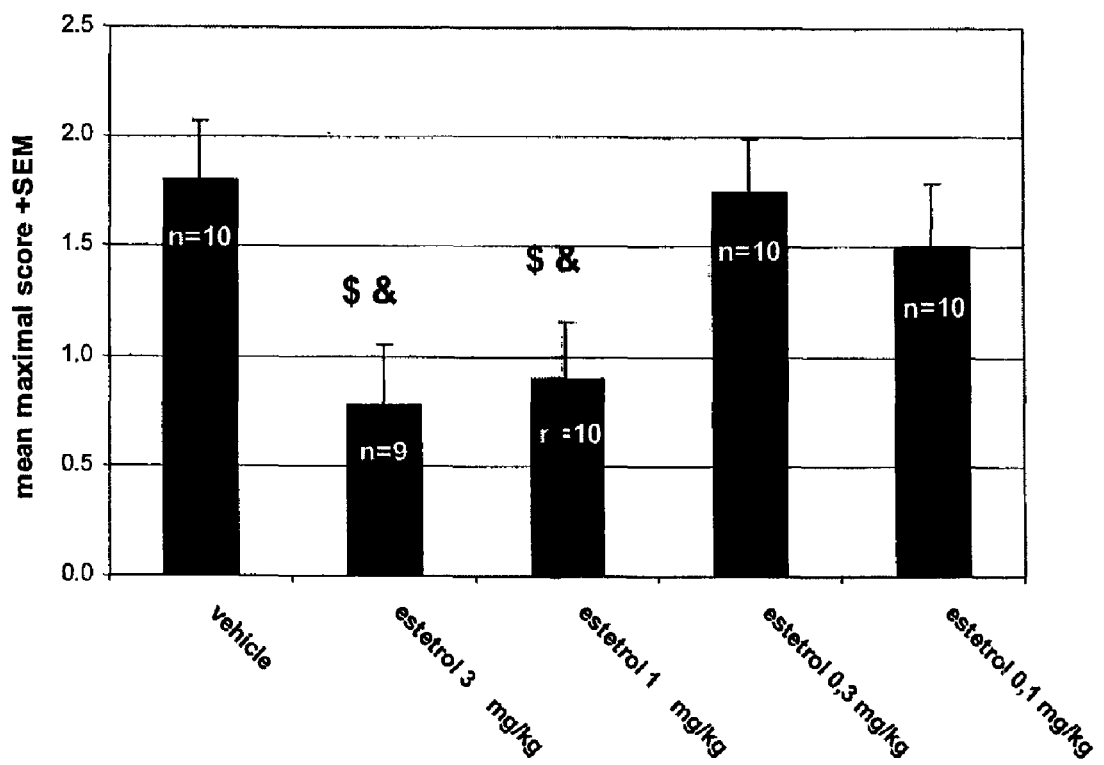
FIG. 3 is a graph showing the effect of treatment with estetrol on the maximal EAE score in SJL/J mice. "$" indicates P=0.011 (estetrol 3 mg/kg) and P=0.021 (estetrol 1 mg/kg) as compared to vehicle. "&" indicates P=0.016 (estetrol 3 mg/kg) and P=0.029 (estetrol 1 mg/kg) as compared to estetrol 0.3 mg/kg.

For each individual mouse the maximal clinical score during the entire monitoring period was assessed, after which the individual data were included in the group mean (FIG. 3). The mean maximal clinical score for vehicle-treated mice was 1.8±0.3. Treatment with 3 and 1 mg/kg estetrol suppressed the mean maximal disability score and resulted in scores of 0.8±0.3 and 0.9±0.3, respectively. Treatment with the two lowest dosages estetrol (0.3 and 0.1 mg/kg) did not show statistically significant differences as compared to vehicle-treated mice. Based on the ANOVA comparison between treatment groups and post-hoc LSD analysis, it is therefore concluded that oral treatment with estetrol results in statistically significant inhibition of EAE's maximal disability score in a dose-dependent fashion as compared to vehicle-treated mice (P=0.011 and P=0.021 for estetrol 3 mg/kg and 1 mg/kg, respectively).

Figure 4:
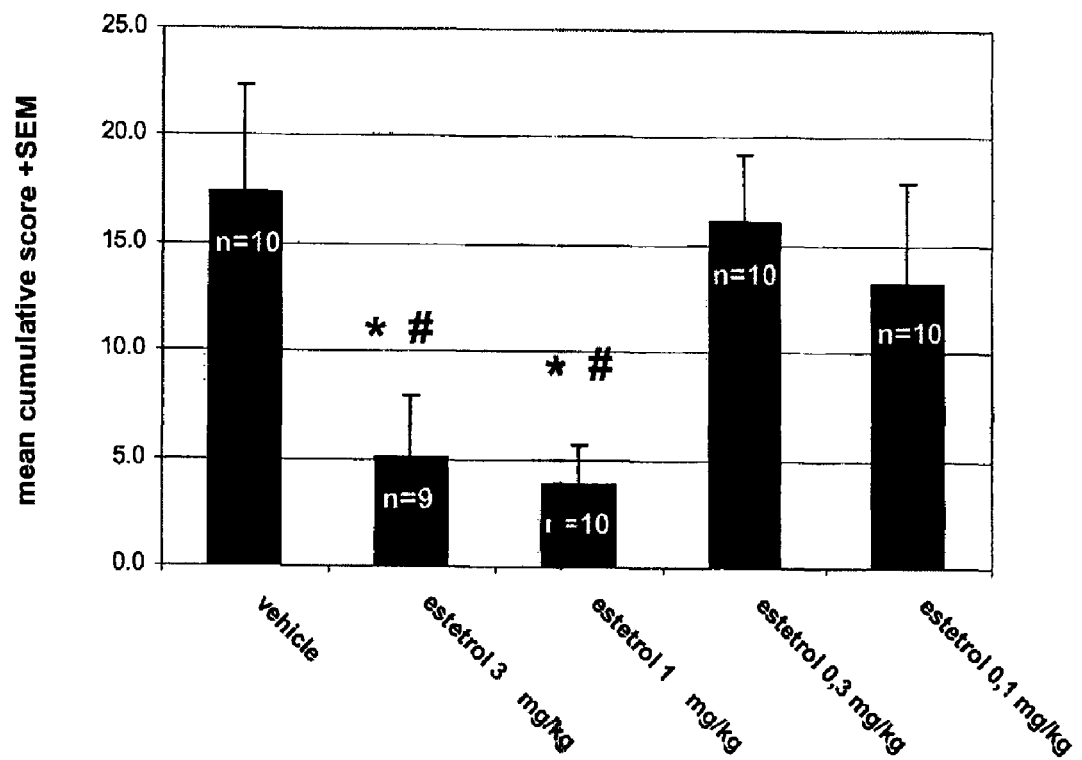
FIG. 4 is a graph showing the effect of treatment with estetrol on the cumulative clinical EAE score (day 0-42) in SJL/J mice. "*" indicates P=0.025 (estetrol 3 mg/kg) and P=0.012 (estetrol 1 mg/kg) as compared to vehicle. "#" indicates P=0.042 (estetrol 3 mg/kg) and P=0.022 (estetrol 1 mg/kg) as compared to estetrol 0.3 mg/kg.

The most relevant clinical outcome of the study, i.e. the cumulative disability scores of individual mice are presented as group means in FIG. 4 for the complete monitoring period (day 0-42). When analyzed over the entire treatment and monitoring period vehicle-treated mice developed a mean cumulative EAE of 17.4±5.0, whereas treatment with 3 and 1 mg/kg estetrol suppressed the mean cumulative EAE score to 5.8±2.9 and 3.9±1.8, respectively (FIG. 3). Treatment with the two lowest dosages estetrol (0.3 and 0.1 mg/kg) did not show statistically significant differences as compared to vehicle-treated mice. Based on the ANOVA comparison between treatment groups and post-hoc LSD analysis, it is therefore concluded that oral treatment with estetrol shows statistically significant inhibition of EAE's cumulative disability score in a dose-dependent fashion as compared to vehicle-treated mice (P=0.025 and P=0.012 for estetrol 3 mg/kg and 1 mg/kg, respectively).

Figure 5:
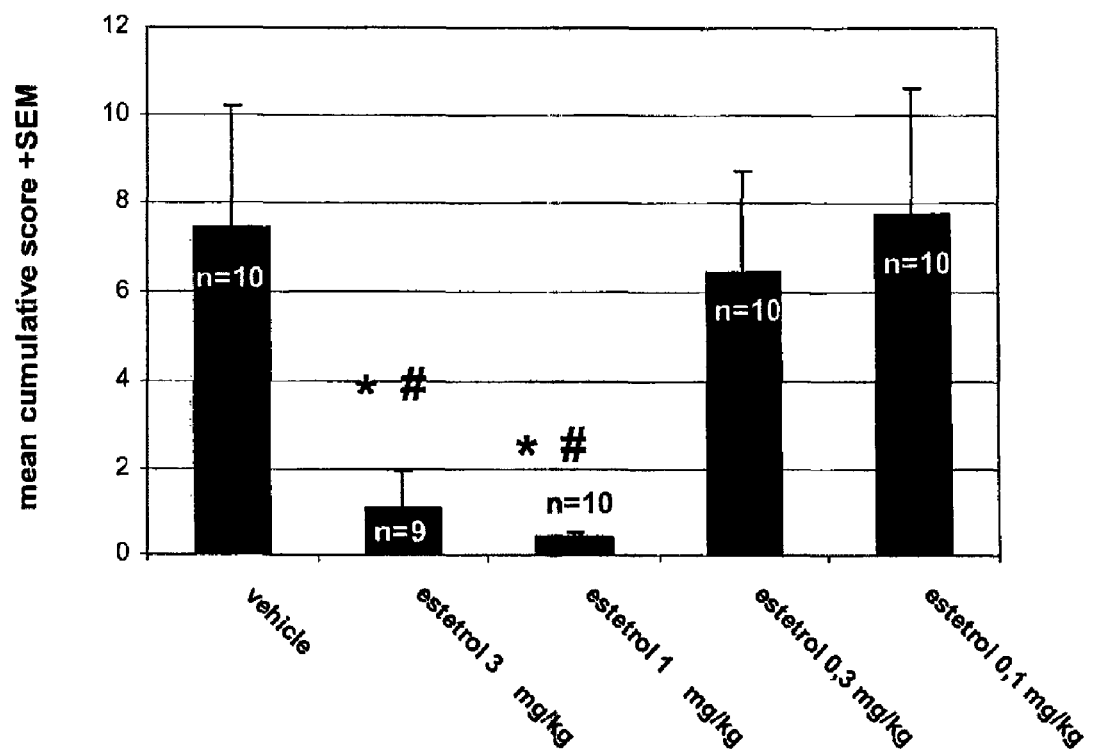
FIG. 5 is a graph showing the effect of treatment with estetrol on the cumulative clinical EAE score in the relapsing phase (day 26-42) in SJL/J mice. "*" indicates P=0.045 (estetrol 3 mg/kg) and P=0.023 (estetrol 1 mg/kg) as compared to vehicle. "#" indicates P=0.050 (estetrol 3 mg/kg) and P=0.018 (estetrol 1 mg/kg) as compared to estetrol 0.3 mg/kg.

As is typical for the PLP$_{139-151}$ EAE model in SJL/J mice, a substantial amount of control mice that were only treated with vehicle developed a second disease episode (relapse). Evaluation of the second phase of disease activity, i.e. the clinical EAE score from day 26 until day 42, showed that mice treated with 3 mg/kg and 1 mg/kg estetrol displayed little evidence of disease activity as opposed to vehicle-treated mice and the other treatment groups (FIG. 5). Based on the ANOVA comparison between treatment groups and post-hoc LSD analysis, it is therefore concluded that oral treatment with estetrol shows statistically significant inhibition of EAE relapses in a dose-dependent fashion as compared to vehicle-treated mice (P=0.045 and P=0.023 for estetrol 3 mg/kg and 1 mg/kg, respectively).

These data show that estetrol, administered orally in an amount effective to also modify endocrine parameters (especially vaginal cornification), surprisingly suppresses the clinical development of EAE. Moreover, estetrol alleviates symptoms in animals that are affected by EAE and prevents animals from developing a disease relapse with severe disease symptoms.

Example 7

The ability of estetrol (E4) to alleviate the symptoms and severity of immune mediated disorders is evaluated in B10.PL mice with experimental autoimmune encephalomyelitis (EAE), an inflammatory disease triggered by the induction of autoreactive T lymphocytes and widely studied as a model of multiple sclerosis (MS) in humans.

Female B10.PL mouse, at an age of 8-12 weeks, are obtained from Jackson Laboratories (Bar Harbor, Me.) and divided into treatment groups of 12 mice. Three days prior to EAE disease induction, animals are anesthetized using a ketamine/xylazine anesthetic mixture and are ovariectomized. The ovaries are removed after a single incision through the back skin and a bilateral flank incision through the peritoneum.

Myelin basic protein (MBP) is isolated from guinea pig spinal cords following the procedure of Deibler, et al. (Deibler, G. E., et al., Prep. Biochem. 2:139, 1972). MBP is stored lyophilized at −20° C. and is dissolved, before use, in 0.1M acetic acid at a concentration of 8 mg/ml. For immunisations, MBP is emulsified in an equal volume of complete Freund's adjuvant (CFA) containing *Mycobacterium tuberculosis* H.sub.37 Ra (4 mg/ml).

To induce EAE, mice are immunised in the skin at the base of the tail with 400 µg MBP in an emulsion of CFA (0.1 ml), containing *Mycobacterium tuberculosis* H.sub.37 Ra. Immediately after the MBP immunisation and 48 hours later, mice are additionally injected intraperitoneally with 200 ng of pertussis toxin (Sigma, St. Louis, Mo.). The mice are examined daily for clinical signs of EAE for 40 days and disease symptoms are scored according to Clayton et al. (J. Exp. Med. 169:1681, 1989): 0: no paralysis, 1: tail limp/slow/dull eyes, 2: partial hind paralysis or limb weakness, 3: difficulty turning over, severe limb weakness or mild paralysis, 4: severe to total paralysis, 5: moribund/dead.

The study comprises a combined prevention/therapeutic protocol, in which the mice are administered various amounts of E4, starting at day 1 of the study (day of MBP-immunisation) until and including day 40. Four groups of mice are orally treated once daily with E4 (0.1, 0.3, 1.0 or 3.0 mg/kg/day) and one group of mice, receiving once daily oral vehicle treatment (hydroxy propyl-beta-cyclodextrin 20% wt/vol) as a negative control. Similarly, the study further comprises 4 groups of mice subcutaneously treated once daily with E4 (0.1, 0.3, 1.0 or 3.0 mg/kg/day) and one group of mice, receiving once daily subcutaneous vehicle treatment (hydroxy propyl-beta-cyclodextrin 20% wt/vol) as a negative control.

Neither oral nor subcutaneous treatment with vehicle is effective in preventing EAE disease development in MBP immunised mice. Typically, animals show a rapid onset of disease symptoms and progessively develop more signs of autoimmune disease over the evaluation period. At 40 days, most animals suffer from severe forms of EAE (typically grading as 3 or more). Interestingly, subcutaneous and oral E4 treatment show dose-dependent effects in delaying the onset of EAE disease symptoms and prevent a severe development of autoimmune disease over a 40 days evaluation period. Comparison of the treatment groups with the control groups reveals that the number of afflicted animals and/or severity of EAE symptoms are dose-dependently reduced over the dose range tested in E4-treated mice.

The study is repeated separately with non-castrated female B10.PL and male B10.PL mouse, demonstrating again E4's ability to dose-dependently alleviate symptoms and severity of EAE after daily subcutaneous and/or oral administration.

Example 8

The ability of estetrol to alleviate the severity of immune mediated disorders and its possible side-effects were evaluated and compared with dexamethasone in mice developing collagen induced arthritis (CIA), which is another experimental system of autoimmune and chronic inflammatory disease, representing human arthritic diseases, particularly rheumatoid arthritis (RA).

Arthritis was induced in male DBA/1 mice using a two-step immunization protocol (Joosten et al., "Dual role of IL-12 in early and late stages of murine collagen type II arthritis". J Immunol 1997; 159:4094-4102; Joosten et al., "IL-1β blockade prevents cartilage and bone destruction in murine type II collagen-induced arthritis, whereas TNFα blockade only ameliorates joint inflammation". J Immunol 1999; 163:5049-55). This strain is highly susceptible to CIA induced with bovine type II collagen. On day 0, mice were immunized with bovine type II collagen (100 µg) emulsified in Freund's complete adjuvant (four subcutaneous injections in the back). On day 21, mice were boosted with an i.p. injection of 100 µg collagen type II diluted in PBS.

The effect of oral treatment with estetrol on collagen-induced arthritis was studied in a 6-week study design. From day 22 until the end of the study (day 42), the animals were treated once daily with vehicle (hydroxypropyl-beta-cyclo-dextrin in a 20% wt/vol solution in water) serving as negative control or four different dosages of estetrol (3 mg/kg, 1 mg/kg, 0.3 mg/kg and 0.1 mg/kg). Dexamethasone (1 mg/kg), was chosen as a positive control because it is a well studied corticosteroid that reduces swelling and inflammation and is used in a variety of disorders such as skin diseases (psoriasis, hives), allergic conditions, breathing problems, cancer, blood disorders (anemia), digestive problems, eye disorders and for the treatment of arthritis. Although effective as an anti-inflammatory agent, dexamethasone is also known to induce a number of side effects, which amongst others include in humans the induction of osteoporosis, reduced adrenal function, dizziness, nausea, indigestion, increased appetite, weight gain due to enhanced water retention, weakness and/or sleep disturbances. In addition, systemic dexamethasone treatment in rodents results in strong catabolic effects that can be easily observed as weight loss (Orzechowski et al. 2002, "Rats with a glucocorticoid-induced catabolic state show symptoms of oxidative stress and spleen atrophy: the effects of age and recovery". J Vet Med A Physiol Pathol Clin Med; 49:256-63).

All groups used in the study consisted of 13 mice. During the study animals were weighed and monitored for clinical signs of arthritis. Scoring of disease severity (clinical arthritis score) was performed according to scoring system described by Joosten et al. 1997 (J. Immunol., 159:4094-4102) and Joosten et al. 1999 (J. Immunol., 163:5049-55).

Basic statistical analyses were performed as follows: The significance of differences between all treatment groups in the main clinical outcome parameters was tested using analysis of variance (ANOVA). Each significant ANOVA was followed by post hoc Tukey tests to determine the significance of the difference between each treatment group and the control group. Furthermore, linear regression analysis was used to study the dose-dependency of the effects of treatment with estetrol. All statistical analysis were performed using statistical software program SPSS 10.0 for Windows (SPSS Inc., Chicago, Ill., USA).

Figure 6:
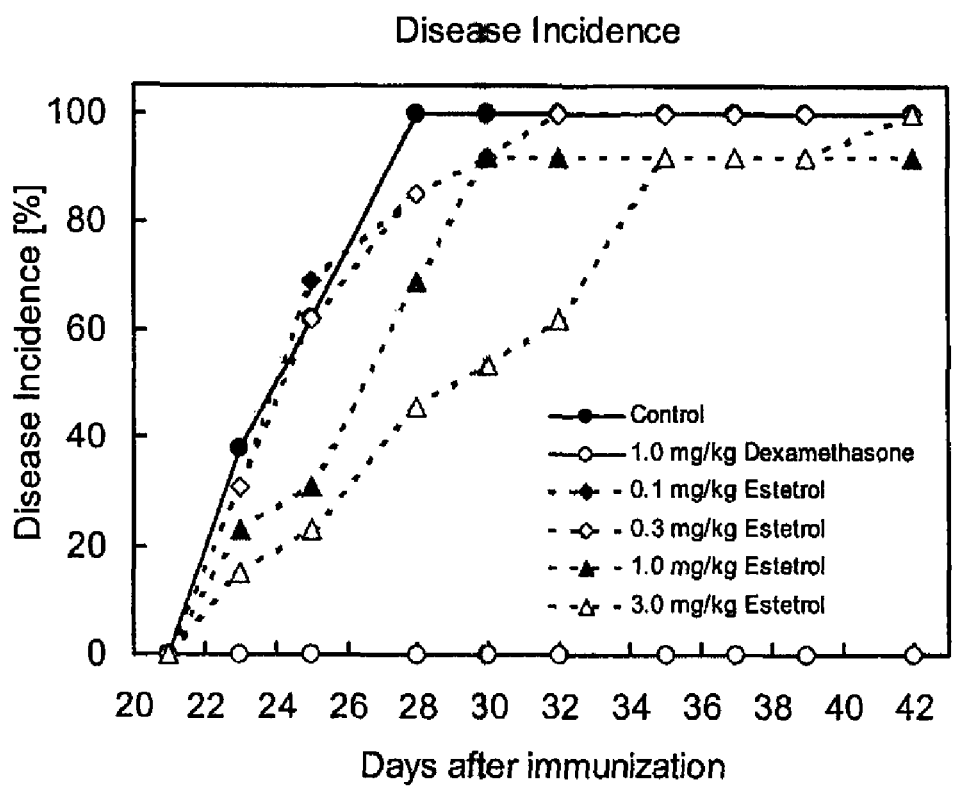
FIG. 6 is a graph showing the effect of treatment with estetrol on disease incidence for all studied treatment groups versus time. "Disease" was defined as a macroscopic arthritis score of >0.

Vehicle-treated animals (controls) all developed arthritis soon after the second immunization with collagen type II on day 21. The mean day of disease onset for vehicle-treated mice was 25.4±0.64 days and reaching a disease incidence of 100% on day 28 (FIG. 6). Following the booster on day 21, none of the dexamethasone-treated animals (positive control) developed arthritis before the end of the study. For this treatment group, disease incidence was 0% up to day 42 (FIG. 6). Treatment with estetrol dose-dependently postponed the average day of disease onset to day 25.8, 26.0, 28.2, and 30.7 for the 0.1, 0.3, 1.0 and 3.0 mg/kg estetrol treatment groups. This effect is also seen in FIG. 6, in which the increase in disease incidence is clearly delayed in the 1.0 mg and 3.0 mg/kg estetrol groups as compared to the control group of vehicle-treated animals.

Figure 7:
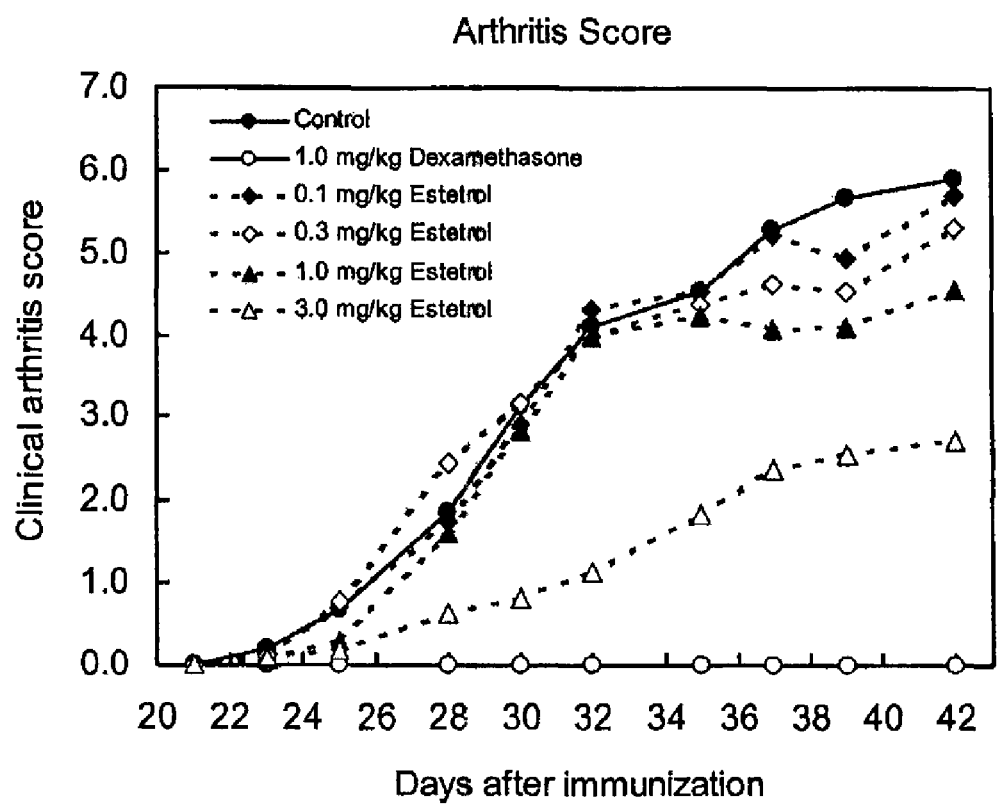
FIG. 7 is a graph showing the effect of treatment with estetrol on macroscopical arthritis score in mouse CIA. Each point represents the group mean (n=13).
Figure 8:
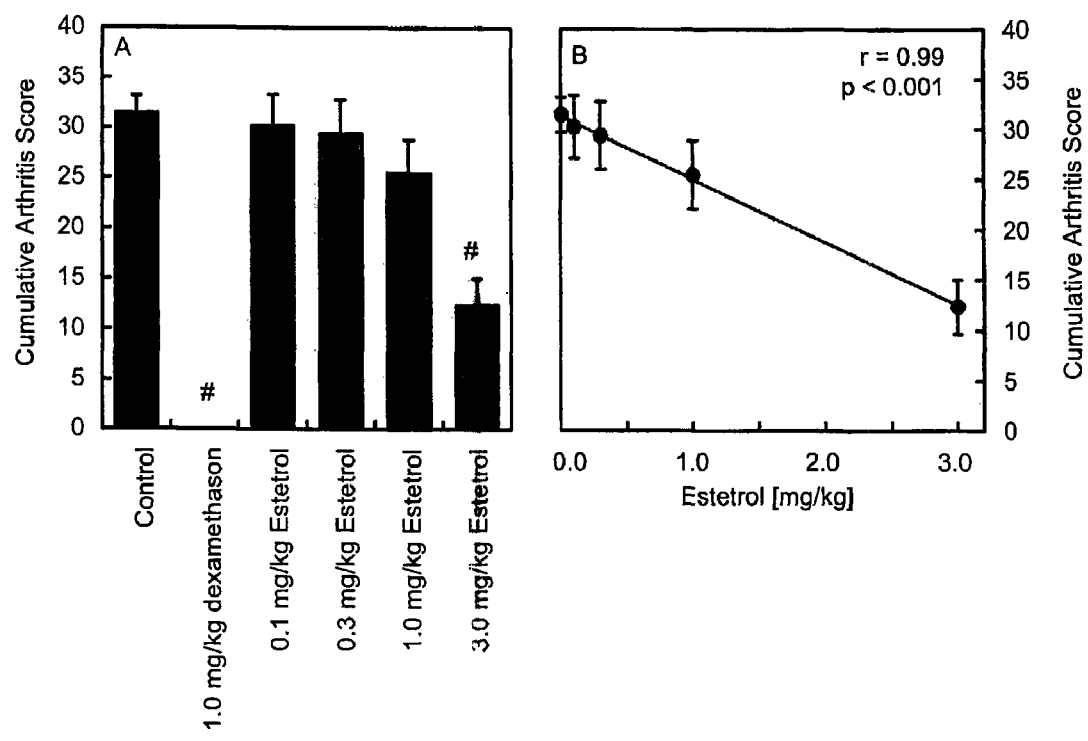
FIGS. 8A and 8B are graphs showing the effect of treatment with estetrol on the cumulative arthritis score in mouse CIA. For each mouse, the cumulative score was calculated by summing the scores obtained at each of the 10 time points. Panel A: group data are presented as mean±SEM (n=13). Panel B: Linear regression of Estetrol dose versus Cumulative arthritis score. #, indicates p<0.001 versus control, based on ANOVA and Tukey post hoc test.

The macroscopic arthritis score steadily increased with time in vehicle-treated mice, reaching a mean score of 5.90±0.38 on day 42 (FIG. 7). Over the entire monitoring period the average cumulative arthritis score (day 21 to 42) in vehicle-treated mice was 31.4±1.73 (FIG. 8). Since no disease developed in dexamethasone-treated animals, the macroscopic arthritis score remained 0 until day 42 (FIG. 7). Consequently, the average cumulative arthritis score (day 21 to 42) in dexamethasone-treated animals was also 0 (FIG. 8). Further in line with the delayed incidence of arthritis, also development of macroscopical arthritis score was dose-dependently reduced in the mice receiving estetrol (FIG. 7). Similarly, the average cumulative arthritis score (day 21 to 42) in estetrol-treated animals was dose-dependently reduced and significantly different as compared to vehicle-treated animals (FIGS. 8A and 8B).

Figure 9:
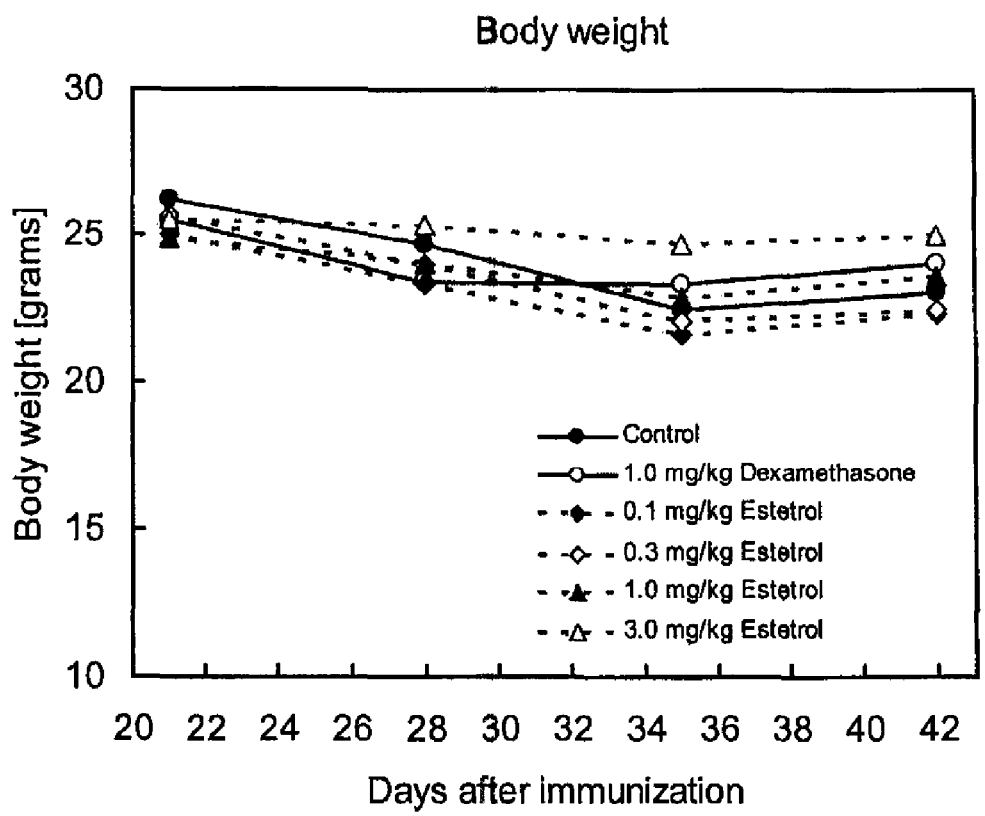
FIG. 9 is a graph showing the effect of treatment with estetrol on body weight in mouse CIA. The mice were weighed per group on days 21, 28, 35, and 42.

As an additional clinical endpoint for disease severity and/or drug-induced side-effects body weights were measured on a weekly basis. The body weight of the vehicle-treated animals (negative control) decreased to 94.2%, 85.7% and 87.9% of their initial weight (at day 21) on days 28, 35 and 42, respectively (FIG. 9). Following treatment with dexamethasone, the body weight of the mice also decreased to 91.5%, 91.4% and 94.0% of their initial weight (day 21) on days 28, 35 and 42, respectively (FIG. 9). Weight loss in mice treated orally with estetrol was comparable to the negative and positive control animal groups for the lower three doses (0.1, 0.3 and 1.0 mg/kg). However, the highest estetrol dose (3.0 mg/kg) protected mice against weight loss: the body weight of the mice in this group only decreased to 99.3%, 96.7% and 97.9% of their initial weight (day 21) on days 28, 35 and 42, respectively (FIG. 9), indicating that neither arthritis nor drug-induced side-effects (as for example seen with dexamethasone) negatively affected the animals treated with the 3.0 mg/kg dose.

In conclusion, these data show that estetrol administered orally in an amount effective to also modify endocrine parameters (e.g. vaginal cornification) surprisingly suppresses the development of arthritis as well as the severity of arthritis in CIA. As such estetrol may be a therapeutic modality for treatment of arthritis without exhibiting the side-effects as seen with currently existing drugs e.g. dexamethasone.

Example 9

The ability of estetrol (E4) to alleviate the symptoms and severity of immune mediated disorders is further evaluated in ovariectomized mice developing collagen induced arthritis (CIA).

Female DBA-1 mice at an age of 8-12 weeks at the start of the experiments are divided into treatment groups of 12 mice. Three days prior to CIA disease induction, animals are anesthetized using a ketamine/xylazine anesthetic mixture and ovariectomized. The ovaries are removed after a single incision through the back skin and a bilateral flank incision through the peritoneum.

Bovine type II collagen (CII) is isolated and purified according to the protocol of Wooley et al. (J. Exp. Med. 154: 688-700, 1981). Before use, CII is first dissolved in 0.1M acetic acid at a concentration of 2 mg/ml and then emulsified 1:1 with complete Freund's adjuvant (CFA) containing *Mycobacterium tuberculosis* H.sub.37 Ra (4 mg/ml) or, for booster immunisation, emulsified 1:1 with incomplete Freund's adjuvant (IFA).

To induce CIA, mice are immunised with 0.1 ml of the emulsion prepared in CFA at the base of the tail. Twenty-one days later, the animals receive a booster injection of 0.1 ml of the emulsion prepared in IFA. The mice are examined daily for clinical signs of CIA from the beginning of the experiment until the termination at day 60 after the first immunisation. Clinical signs of CIA are scored according to Wooley et al. (J. Exp. Med. 154: 688-700, 1981), using a scale from 0 to 3 for each paw: 0: no arthritis; 1: redness and swelling in the paw or toes; 2: severe swelling or deformity in the paw and 3: ankylosis. An arthritic score for each mouse is obtained by summing the score of all paws. For each mouse, the possible severity as measured by the arthritic score may range from 0 to 12.

A combined prevention/therapeutic protocol is used, in which the mice are administered various amounts of E4, starting at day 1 of the study (day of first CII-immunisation) until and including day 60. Four groups of mice are orally treated once daily with E4 (0.1, 0.3, 1.0 or 3.0 mg/kg/day) and one group of mice, receiving once daily oral vehicle treatment (hydroxy propyl-beta-cyclodextrin 20% wt/vol) as a negative control. Similarly, the study further comprises 4 groups of mice subcutaneously treated once daily with E4 (0.1, 0.3, 1.0 or 3.0 mg/kg/day) and one group of mice, receiving once daily subcutaneous vehicle treatment (hydroxy propyl-beta-cyclodextrin 20% wt/vol) as a negative control.

Neither oral nor subcutaneous treatment with vehicle is effective in preventing CIA disease development in CII immunised mice. Vehicle-treated animals, typically, show a rapid onset of disease symptoms and develop more signs of CIA over the evaluation period. At 60 days, most animals suffer from severe forms of CIA (typically grading as 4 or more). Interestingly, subcutaneous and oral E4 treatment show dose-dependent effects in delaying the onset of CIA symptoms and prevent a progressive development to more severe forms of joint destruction over a 60 days evaluation period. Comparison of the treatment groups with the control groups shows that the number of afflicted animals and/or severity of CIA symptoms are dose-dependently reduced in E4-treated mice.

The study is repeated separately with non-castrated female DBA-1, demonstrating again E4's ability to dose-dependently alleviate symptoms and severity of CIA after daily subcuteneous and/or oral administration.

Example 10

Preparation of 100 Capsules, Containing 2 mg Estetrol and 2 mg Dexamethasone Per Capsule 200 mg estetrol, 200 mg dexamethasone (as di-sodium-phosphate salt) and 75 mg colloidal siliciumdioxide (Aerosil® 200V) are mixed together. The resulting powder mixture is transferred into a beaker with volume indication. Volume is adjusted to 37 ml with microcrystalline cellulose (Avicel® PH102). Subsequently, the powder mixture is filled into 100 two-piece hard gelatine capsules (Capsugel® 2).

Example 11

Preparation of 100 Capsules, Containing 2 mg Estetrol and 3 mg Methotrexate Per Capsule 200 mg estetrol, 300 mg methotrexate (as di-sodium salt) and 75 mg colloidal siliciumdioxide (Aerosil® 200V) are mixed together. The powder mixture thus obtained is transferred into a beaker with volume indication. Volume is adjusted to 37 ml with microcrystalline cellulose (Avicel PH102). The powder mixture obtained is filled into 100 two-piece hard gelatine capsules (Capsugel® 2).

The invention claimed is:
1. A method of treating or reducing the risk of developing an immune mediated disorder in a mammal, said immune mediated disorder being selected from the group consisting of multiple sclerosis; rheumatoid arthritis; and osteoarthritis, and said method comprising administering a therapeutically effective amount of an estrogenic component selected from the group consisting of a substance represented by

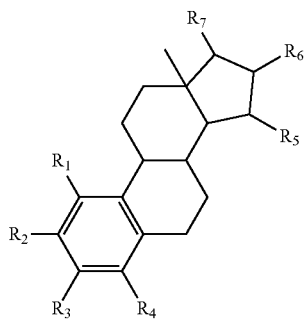

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; no more than 3 of $R_1$, $R_2$, $R_3$, $R_4$ are hydrogen atoms;

precursors capable of liberating a substance according to the aforementioned formula, which precursors are derivatives of the estrogenic substances wherein the hydrogen atom of at least one of the hydroxyl groups has been substituted by an acyl radical of a hydrocarbon carboxylic, sulfonic acid or sulfamic acid of 1-25 carbon atoms; tetrahydrofuranyl; tetrahydropyranal; or a straight or branched chain glycosydic residue containing 1-20 glycosidic units per residue; and mixtures of one or more of the aforementioned substances and/or precursors.

2. The method according to claim 1, wherein $R_3$ represents a hydroxyl group or an alkoxy group.

3. The method according to claim 1, wherein 3 of the groups $R_1$, $R_2$, $R_3$, and $R_4$ represent hydrogen atoms.

4. The method according to claim 1, wherein the estrogenic component exhibits an 8β, 9α, 13β, 14α configuration of the steroid-skeleton.

5. The method according to claim 1, wherein the method comprises the uninterrupted administration of the estrogenic component during a period of at least 5 days.

6. The method according to claim 1, wherein the method comprises oral or subcutaneous administration of the estrogenic component.

7. The method according to claim 6, wherein the method comprises oral administration.

8. The method according to claim 1, wherein the estrogenic component is administered in an amount of at least 1 μg per kg of bodyweight per day.

9. The method according to claim 1, wherein the immune mediated disorder is a T-lymphocyte mediated disorder and/or a chronic inflammatory disease.

10. The method according to claim 9, wherein the immune mediated disorder is a Th1 mediated disorder.

11. The method according to claim 1, wherein estrogenic component is administered orally.

12. The method according to claim 1, wherein the method is for treating the immune mediated disorder in the mammal.

* * * * *